US008562661B2

(12) United States Patent
Lytle et al.

(10) Patent No.: US 8,562,661 B2
(45) Date of Patent: *Oct. 22, 2013

(54) HIGH BLOOD PRESSURE SYMPTOM RELIEF THROUGH A LASER BASED MEDICAL INSTRUMENT

(75) Inventors: Larry Lytle, Rapid City, SD (US); Alf-Kare Eide Riisnaes, Rapid City, SD (US); Kip Lytle, Rapid City, SD (US); Shawn Gab, Rapid City, SD (US)

(73) Assignee: 2035, Inc., Rapid City, SD (US)

( * ) Notice: Subject to any disclaimer, the term of this patent is extended or adjusted under 35 U.S.C. 154(b) by 334 days.

This patent is subject to a terminal disclaimer.

(21) Appl. No.: 12/793,704

(22) Filed: Jun. 4, 2010

(65) Prior Publication Data

US 2011/0301671 A1    Dec. 8, 2011

(51) Int. Cl.
*A61N 5/06* (2006.01)
*A61B 19/00* (2006.01)
*A61B 18/18* (2006.01)

(52) U.S. Cl.
USPC ............... 607/89; 607/88; 128/898; 606/3

(58) Field of Classification Search
USPC ............ 606/2–52; 607/88–93, 23; 128/898
See application file for complete search history.

(56) References Cited

U.S. PATENT DOCUMENTS

| 2004/0006378 A1* | 1/2004 | Shanks et al. | 607/89 |
| 2004/0030370 A1* | 2/2004 | Lytle | 607/89 |
| 2005/0228463 A1* | 10/2005 | Mac et al. | 607/89 |
| 2006/0259021 A1* | 11/2006 | Lin | 606/4 |
| 2010/0168605 A1* | 7/2010 | Aarts | 600/549 |
| 2010/0305667 A1* | 12/2010 | Shou et al. | 607/90 |
| 2011/0040546 A1* | 2/2011 | Gerber et al. | 703/11 |

* cited by examiner

*Primary Examiner* — Dawayne A Pinkney
(74) *Attorney, Agent, or Firm* — Ray Abhyanker, P.C.

(57) ABSTRACT

Disclosed are several methods, apparatus, and a system for providing hypertension/high blood pressure symptom relief through a laser based medical instrument. In one embodiment, a method includes generating a radiation of a laser-light created by a laser diode of a medical instrument. In addition, the method includes applying a treatment of the radiation to a portion of a body. The method further includes regulating of a blood pressure and an advanced glycation end product (AGE) in the blood caused by one of a disease associated with hypertension and blood pressure. Additionally, the method includes providing a relief from high blood pressure when the treatment is complete.

4 Claims, 19 Drawing Sheets

| | |
|---|---|
| DAY 1 | TREATMENT PROVIDED |
| DAY 2 | NO TREATMENT |
| DAY 3 | TREATMENT PROVIDED |
| DAY 4 | NO TREATMENT |
| DAY 5 | TREATMENT PROVIDED |
| DAY 6 | NO TREATMENT |
| DAY 7 | TREATMENT PROVIDED |
| DAY 8 | NO TREATMENT |
| DAY 9 | TREATMENT PROVIDED |

APPLICATION OF Q1000 BASED ON TABLE ABOVE

TREATMENT SCHEDULE 1600

FIGURE 16

| PARTICIPANT | 1 | 2 | 3 | 4 | 5 | 6 | 7 | 8 | AVG |
|---|---|---|---|---|---|---|---|---|---|
| SYSTOLIC-BASE | 127 | 146 | 140 | 138 | 156 | 171 | 160 | 135 | 147 |
| SYSTOLIC-FINAL | 120 | 131 | 128 | 124 | 127 | 154 | 149 | 128 | 133 |
| DIASTOLIC-BASE | 69 | 97 | 92 | 83 | 79 | 95 | 104 | 77 | 87 |
| DIASTOLIC-FINAL | 65 | 84 | 81 | 66 | 66 | 94 | 93 | 68 | 77 |
| PARTICIPANT % INCR/DECR | 1 | 2 | 3 | 4 | 5 | 6 | 7 | 8 | |
| SYSTOLIC | -5.51% | -10.27% | -8.57% | -10.14% | -18.59% | -9.94% | -6.88% | -5.19% | -9.55% |
| DIASTOLIC | -5.80% | -13.40% | -11.96% | -20.48% | -16.46% | -1.05% | -10.58% | -11.69% | -11.35% |

FIGURE 17B

HIGH BLOOD PRESSURE SYMPTOM RELIEF THROUGH A LASER BASED MEDICAL INSTRUMENT

FIELD OF TECHNOLOGY

This disclosure relates generally to the field of medical instruments, and, in one embodiment, to several methods, a system, and apparatus of a laser based medical instrument for providing high blood pressure symptom relief.

BACKGROUND

Hypertension/blood pressure affects millions of people each year. Blood pressure is measured with a blood pressure cuff and recorded as two numbers, such as 120/80 mm Hg (millimeters of mercury).
A top, larger number is called a systolic pressure. This is
 pressure generated when heart contracts (pumps). It reflects the pressure of the blood against arterial walls.
A bottom, smaller number is called a diastolic pressure. This reflects the pressure in the arteries while the heart is filling and resting between heartbeats.

When hypertension/high blood pressure is left untreated, it may lead to heart disease, heart attack, congestive heart failure, stroke, kidney failure, peripheral artery disease, and aortic aneurysms (outpouchings of the aorta).

There are six primary classes of antihypertensive drugs: Thiazide or thiazidelike diuretics act on the kidneys to help rid the body of salt and water through urination. With less fluid in the body, blood volume goes down, which results in a fall in blood pressure. Adverse effects of thiazide diuretics include sexual dysfunction, glucose intolerance, gout, low potassium level (hypokalemia), and low sodium level (hyponatremia). Beta blockers: these drugs may worsen blood glucose control, elevate triglyceride level, and lower high-density lipoprotein (HDL—sometimes called the "good" cholesterol). Angiotensin II receptor blockers (ARBs) work similarly to ACE inhibitors. Adverse effects of ARBs can include headache, drowsiness, diarrhea, and a metallic or salty taste in the mouth. Calcium channel blockers (CCBs) affect a transport of calcium into the cells of the heart and blood vessels, causing blood vessels to relax. Adverse effects of CCBs include constipation, swelling of the lower part of the legs, flushing, or headache. Alpha blockers block alpha receptors in vascular smooth muscle, preventing the uptake of catecholamines, which are produced in response to stress. People using alpha blockers may experience a drop in blood pressure (called orthostatic hypotension) when they go from sitting or lying down to standing. Other common adverse effects include stuffy nose and dizziness.

SUMMARY

Disclosed are several methods, apparatus, and a system for providing hypertension/blood pressure symptom relief through a laser based medical instrument. In one aspect, a method includes generating a radiation of a laser-light created by a laser diode of a first medical instrument. In addition, the method includes applying a treatment of the radiation to a portion of a body. The method also includes regulating one of a blood pressure and an Advanced Glycation End product (AGE) in the blood caused by a disease associated with hypertension and blood pressure. In addition, the method includes providing a reduction from the high blood pressure when the treatment is complete.

The method may include adjusting of a pulsation power, a pulsation frequency, and/or pulsation duration of the radiation to provide the treatment. The wavelength of the radiation may be adjusted by using different laser diodes. The method may further include enabling of the laser diodes to adjust the wavelength of the radiation to provide the treatment. The method may also include applying the radiation to an application point between 1-9 days. In addition, the method may include coordinating a delivery of a soliton wave when the radiation of the laser-light is applied. The method may further include coupling the first medical instrument to a second medical instrument. The method may also include generating a first soliton wave through the first medical instrument at a first wavelength and at a first frequency. In addition, the method may include generating a second soliton wave through the second medical instrument at a second wavelength and at a second frequency. The method may also include coordinating the delivery of the first soliton wave and the second soliton wave on a biological medium through an algorithm that controls delivery of laser and diode light of the first medical instrument and the second medical instrument.

In addition, the method may include authenticating the medical instrument based on an identifier associated with the medical instrument using a processor. The method may also include authenticating a user of the medical instrument based on a password using the processor and generating a graphical representation of the medical instrument. The method may further include providing a set of rules associated with the medical instrument based on the identifier and/or the user. The method may also include generating a custom mode of operation of the medical instrument based on a response of the user and creating a name associated with the custom mode of operation. The method may include automatically programming the medical instrument based on the custom mode and/or sharing the custom mode with other users and the other medical instruments based on the set of rules and/or a preference of the user (e.g., through a social networking web site). The method may include providing a relief to the patient suffering from hypertension/blood pressure every other day up to sixty days.

In another aspect, a method includes generating a radiation of a laser-light created by a laser diode. The method also includes applying a treatment of the radiation to a portion of a body part. The method further includes reducing a condition in a body of one of reduction in a blood glucose level, a blood glycosylated hemoglobin level (HbA1c), a blurred vision, a weakness, a double vision, a cramp, a shortness of breath, an abdominal pain and/or a leg pain. In addition, the method also includes providing a relief from the condition when the treatment is complete.

The method may include adjusting one of a pulsation power, a pulsation frequency, and/or pulsation duration of the radiation to provide the treatment. The method may further include coordinating a delivery of a soliton wave when the radiation of the laser-light is applied. The method may also include adjusting one of the pulsation power, the pulsation frequency, and/or the pulsation duration of the radiation to provide a treatment with a custom mode. In addition, the method may include adjusting of the pulsation power, the pulsation frequency, and/or the pulsation duration of the laser-light radiation to provide additional treatment with a preconfigured mode. The method further may include providing relief from hypertension/blood pressure.

In yet another aspect, a method includes generating a radiation of a laser-light created by a laser diode. In addition, the method includes monitoring the radiation. The method also includes applying a treatment of the radiation to a portion of a body part. The method further includes reducing a blood parameter and/or a secondary complication of a disease. In addition, the method also includes providing a relief from a condition when the treatment is complete.

The method may include adjusting a pulsation power, a pulsation frequency, and/or pulsation duration of the radiation to provide the treatment. The method may also include coordinating a delivery of a soliton wave. In addition, the method may include adjusting one of the pulsation power, the pulsation frequency, and/or the pulsation duration of the radiation to provide the treatment with a custom mode. The method may also include using light emitting diode to monitor the radiation.

BRIEF DESCRIPTION OF THE DRAWINGS

Example embodiments are illustrated by way of example and are not limited to the figures of accompanying drawings, in which like references indicate similar elements and in which:

FIG. 16 illustrates a treatment schedule, according to one or embodiments.

FIG. 17B illustrating the values of the hypertension/blood pressure study results for 8 patients.

Other features of the present embodiments will be apparent from accompanying drawings and from the detailed description that follows.

DETAILED DESCRIPTION

Example embodiments, as described below, may be used to provide several methods, a system, and apparatus of a laser based medical instrument for reducing Hypertension/blood pressure. Although the present embodiments have been described with reference to specific example embodiments, it will be evident that various modifications and changes may be made to these embodiments without departing from the broader spirit and scope of the various embodiments.

Figure 1:
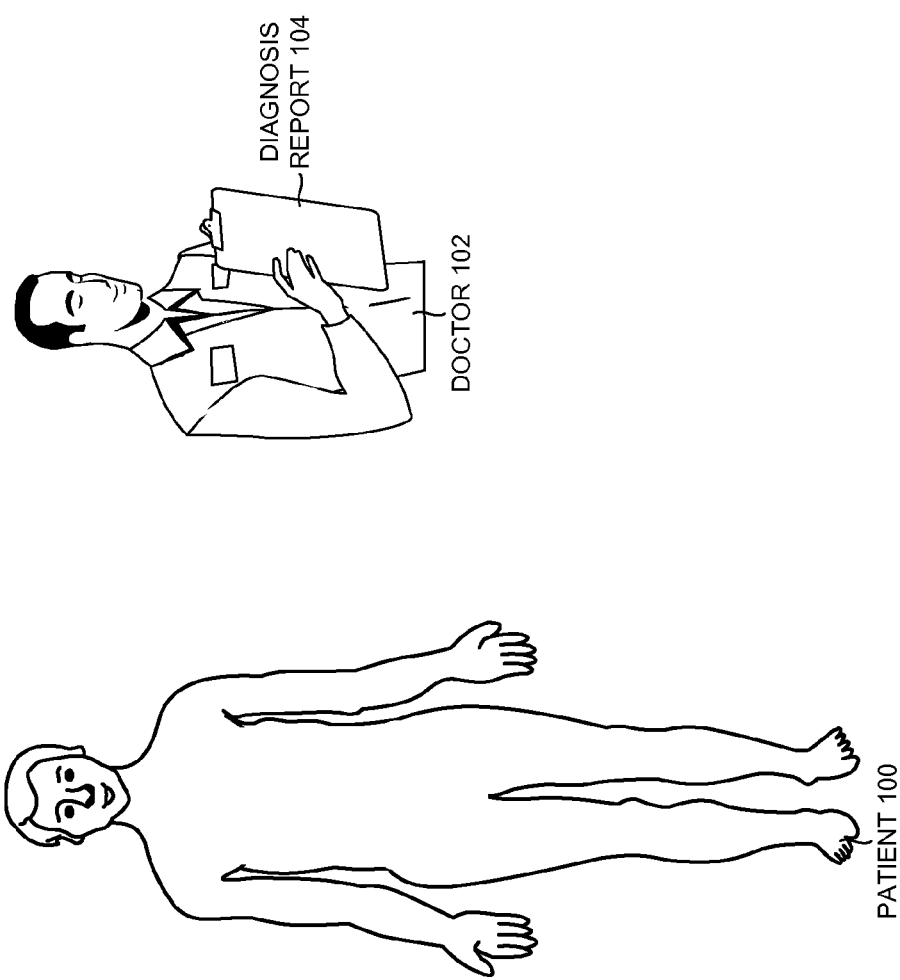
FIG. 1 illustrates a patient and a doctor diagnosing the patient, according to one or more embodiments.

FIG. 1 illustrates a patient 100 and a doctor 102 diagnosing the patient 100, according to one or more embodiments. The patient 100 may be an individual suffering from very high levels of advanced glycation end products (AGE) in the blood and elevated blood pressure. In one embodiment, the patient 100 may be suffering from hypertension/high blood pressure. The vascular diseases, hypertension and atherosclerosis, affect millions of individuals worldwide, and account for a large number of deaths globally. Hypertension and atherosclerosis may be characterized by insulin resistance that plays a major role in their etiology. The cause of insulin resistance is not known, but may be a result of a combination of genetic and lifestyle factors. In insulin resistance, alterations in glucose and lipid metabolism lead to the production of excess aldehydes including glyoxal and methylglyoxal. These aldehydes react non-enzymatically with free amino and sulfhydryl groups of amino acids of proteins to form stable conjugates called advanced glycation end products (AGEs). AGEs act directly, as well as via receptors to alter the function of many intra- and extracellular proteins including antioxidant and metabolic enzymes, calcium channels, lipoproteins, and transcriptional and structural proteins. This results in endothelial dysfunction, inflammation and oxidative stress. All these changes are characteristic of hypertension and atherosclerosis. Human and animal studies have demonstrated that increased AGEs are also associated with these conditions. A pathological role for AGEs is substantiated by studies showing that therapies that attenuate insulin resistance and/or lower AGEs, are effective in decreasing oxidative stress, lowering blood pressure, and attenuating atherosclerotic vascular changes. The AGEs are responsible for various biochemicals in tissues which can lead to development of several complications in arteries including, but not limited to, aortic stiffness independent of age and blood pressure.

The monocyte macrophage plays an important role in this process both by removing the senescent molecules that have accumulated AGEs over time and by initiating the steps that lead to new protein synthesis and tissue remodeling. By regulating the amounts of active macrophages via laser-light radiation, it is possible to regulate blood glucose and AGE breakdown and prevent development of complications from hypertension/blood pressure. The doctor 102 may diagnose the patient 100 to generate a diagnosis report 104. The diagnosis report 104, inter alia may include provide information about symptoms associated with the hypertension/high blood pressure such as headache, dizziness, blurred vision, nausea, palpitation, chest pain and fatigue.

The doctor 102 may use the diagnosis report 104 to determine a type of treatment for the patient 100. In one or more embodiments, the patient 100 may choose a treatment using a set of substantially similar medical instruments described herein.

FIG. 2A-D illustrates a treatment being provided to a patient. The patient described herein may be suffering from hypertension/high blood pressure. A medical instrument 200A-N may include a set of laser diodes 202 for generating radiation and an etched warning indicator 218 for indicating time for providing a treatment. A radiation 204 generated by the medical instrument may be applied on an application points 208A-D. In one or more embodiments, treatment may be provided by applying the radiation 204 generated from the medical instruments 200A-N to the application point's 208A-D. Application points as described herein may include proprioceptive points, acupoints, pressure points and other points. The radiation 204 as discussed herein may be an energy that is transmitted in the form of soliton waves. The soliton waves may be a self-reinforcing solitary wave that maintains its shape while travelling at a constant speed. The laser diodes 202 may be a semiconductor device that produces coherent radiation in which the waves are all at the same frequency and phase. In one or more embodiments, the medical instrument 200A-N may be configured to adjust one or more of a pulsation power, a pulsation frequency and pulsation duration of the radiation 204 to provide treatment. In one or more embodiments, the pulsation power, the pulsation frequency and the pulsation duration of the radiation 204 may be adjusted to a wavelength of the radiation to provide the treatment.

Figure 2A:
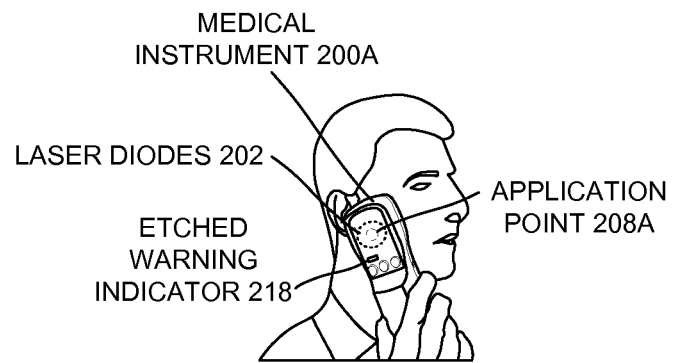
FIG. 2A-D illustrates a treatment being provided to the patient suffering from hypertension/high blood pressure, according to an example embodiment.
Figure 2B:
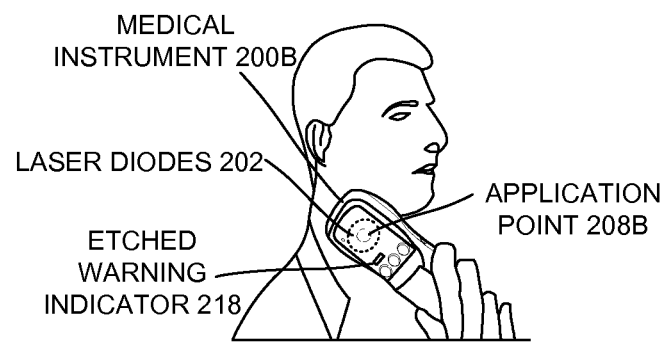
Figure 2C:
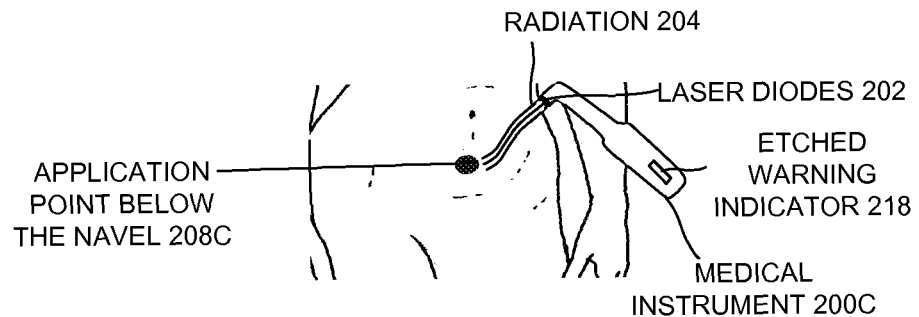

FIG. 2A illustrates treatment being provided by application of a radiation on an application point 208A. Application point's 208A-N as described herein may refer to specific points in body through which radiation may be provided to provide relief from hypertension/high blood pressure. In one or more embodiments, one of the application point 208A for providing a treatment for hypertension/high blood pressure may be in front of the left ear over the Temporomandibular Joint (TMJ) of the patient 100. The radiation (not shown in Figure) generated from the medical instrument 200A may be applied on the application point 208A just in front of the left ear over the TMJ of the patient 100 to provide relief from hypertension/high blood pressure. The application point 208A as illustrated is the joint between the base of the skull and the lower jaw. In one or more embodiments, the medical instrument 200A may be also be used for treatment in general conditions. FIG. 2B illustrates a delivery of the radiation (not shown in Figure) from the medical instrument 200B to an other application point 208B that may be under the angle of the jaw with the laser radiation directed upwards at a 45 degree angle towards the application point 208B to provide the treatment. Similarly, as illustrated in FIG. 2C, the radiation 204 generated from the medical instrument 200C may be delivered to an other application point 208C that may be to a spot one hand width below and in line with the navel to provide relief to the patient from hypertension/high blood pressure. In one or more embodiments, where there is requirement of directed, high-power dosage in a narrow region of a biological medium, a second medical instrument 200C may be used (e.g., a probe device).

Figure 2D:
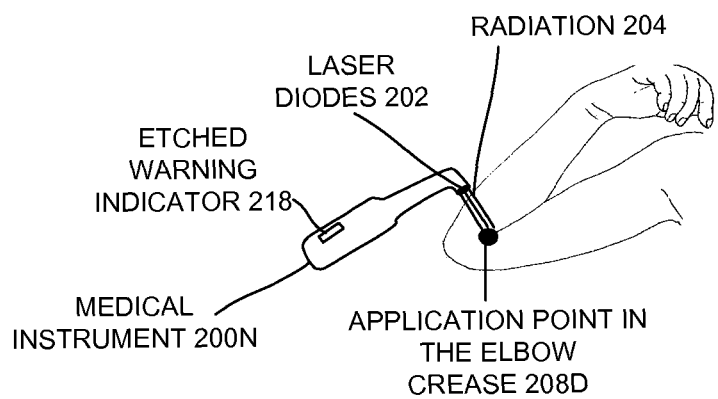

FIG. 2D illustrates a delivery of the radiation 204 through the medical instrument 200N to a different application point 208D at a location at the extreme end of the inner crease of the elbow for providing relief. The delivery of the radiation 204 generated from the medical instrument 200A-N to the application point 208A-N on the patient's body may be for specific duration of time and for a suggested course. For example, the treatment for hypertension/high blood pressure may be for one minute, repeated three times. The medical instrument 200A-N may be configured with an etched warning indicator 218. In one or more embodiments, the etched warning indicator 218 may be used to monitor the radiation 204. When the medical instrument 200A-N is emitting radiation 204, the etched warning indicator 218 may be configured to illuminate. The etched warning indicator 218 may emit light for a duration configured for the treatment, thereby indicating a user to apply the radiation using the medical instrument 200A-N on the application point's 208A-N for the prescribed amount of time. The radiation 204 may be applied to the application points between 1-9 days. In one or more embodiments, the radiation generated by the medical instruments 200A and 200B illustrated in FIG. 2A-B may be a low power radiation. In contrast, the radiation 204 generated by the medical instruments 200C and 200N illustrated in the FIG. 2C-D may be a high power radiation. In one or more embodiments, the blood pressure and AGE in the blood caused by a disease associated with hypertension and blood pressure may be regulated by providing radiation at aforementioned application points and at schedule as prescribed.

Figure 3C:
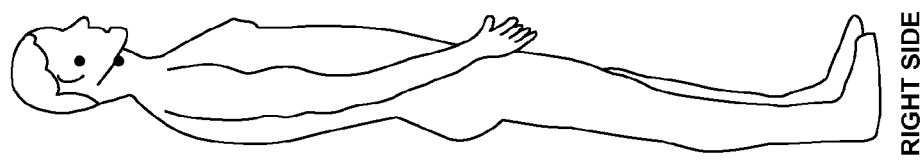
FIG. 3A-C illustrates several application points in a human body for treating hypertension/high blood pressure, according to one or more embodiments.
Figure 3B:
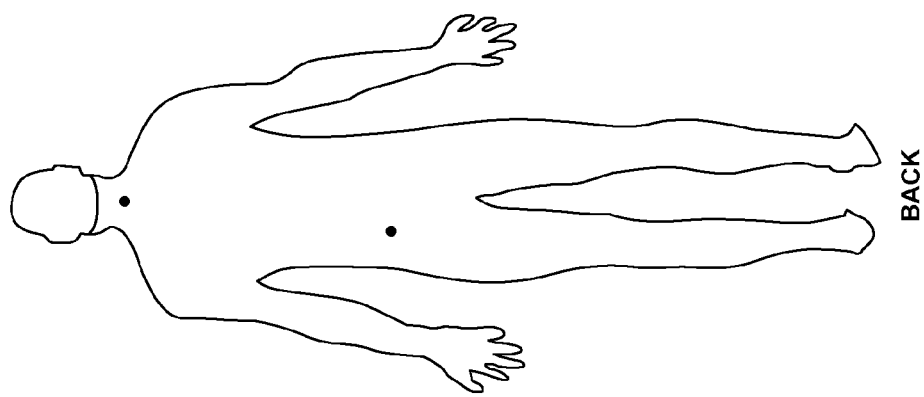
Figure 3A:
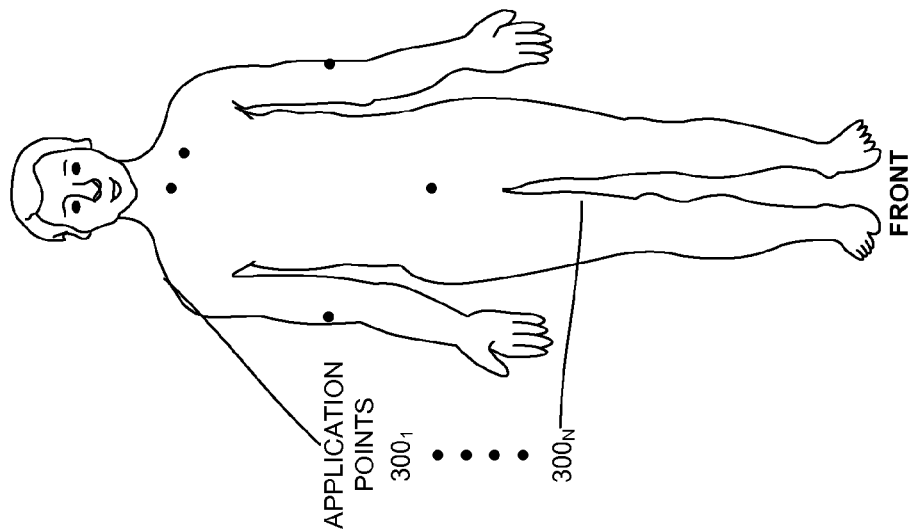

FIG. 3A-C illustrates several application points $300_{1-N}$ in a human body for treating hypertension/high blood pressure. The brain derives much of its feedback information from a process called proprioception. The proprioception is a stimulation of a body tissue to activate protective mechanisms. There are other points such as acupuncture points (also called as acupoints) which are located across anatomy that affect a specific organ. Application points $300_{1-N}$ as described herein may include proprioceptive points, acupoints, pressure points and other points that may be used as treatment points using the medical instruments 200A-N. By activating the application points through the medical instrument (e.g., Q1000® by 2035, Inc.™) the body responds through its voluntary nervous/muscular system, but in an involuntary way. The Central Nervous System is a network of nerve fibers that extend everywhere throughout the human body. These nerve fibers send signals to the organs and muscles, and the nerves and muscles responds to these signals by sending response signals back to the brain. All of this signaling occurs automatically and is not under an individual's conscious control. When the laser (e.g., Q1000® by 2035, Inc.™) is applied to the application points $300_{1-N}$ for approximately one minute, these muscles release and the application signal to the brain changes, which in turn positively affects a Sympathetic and a Parasympathetic divisions of an Autonomic Nervous System. Releasing the Sympathetic division controls stress and subsequently the organ functions improve and the pancreatic function may improve the regulation of insulin.

Proprioception may be defined as the unconscious perception of movement spatial orientation arising from stimuli within the body itself. It is also the body's way of protecting itself. Proprioception directly affects the autonomic nervous system. The autonomic nervous system regulates organ function by coordinating sympathetic and parasympathetic signals. When the sympathetic nervous system is stimulated, there may be increased body activity, increased stress, increased blood pressure, increased heart rate and increased breathing rate. When these areas increase, there may be a simultaneous decrease of glandular, stomach and intestinal function. The body becomes more acidic, goes into a state of oxidation, stress may be increased, and disease may be eminent. If activity in the parasympathetic nervous system increases by stimulation of the body's application points, the opposite happens. The heart and breathing rates slow, blood pressure and acid levels normalize, there may be an increase in the glandular and gut activity, the body reserves increase, and there may be less disease. By balancing the sympathetic and parasympathetic nervous systems there may be less disease. The treatment may be provided by delivering the radiation 204 on the application points $300_{1-N}$. The application points $300_{1-N}$ as described herein as are illustrated in FIG. 3A-C.

FIG. 3A is a front view of the human body illustrating various application points $300_{1-N}$ in the human body that can be used for providing treatment for hypertension/high blood pressure. The application points $300_{1-N}$ as illustrated in the figure may include points but not limited to points over the neck below the Adams apple, over the "V" where the collar bones meet, two finger widths below the collar bone and three finger widths from the arm pit, a spot hand width below and in line with the navel and at the extreme end of the inner crease of the elbows. FIG. 3B is a back view of the human body illustrating an application point for providing radiation 204 that can be used in the treatment of hypertension/high blood pressure. The application point as illustrated may be on a spot over the left kidney in the small of the back approximately one hand width above the belt and one hand width to the left of the spine. In addition, an other application point may be located at back of neck. FIG. 3C is a side view of the human body illustrating the application points that may be just in front of the left ear over the TMJ and under the angle of the jaw with the laser radiation directed upwards at a 45 degree angle (e.g., also illustrated in FIG. 2A-B). Treatment may be provided through application of radiation to various application points in the body.

Figure 4:
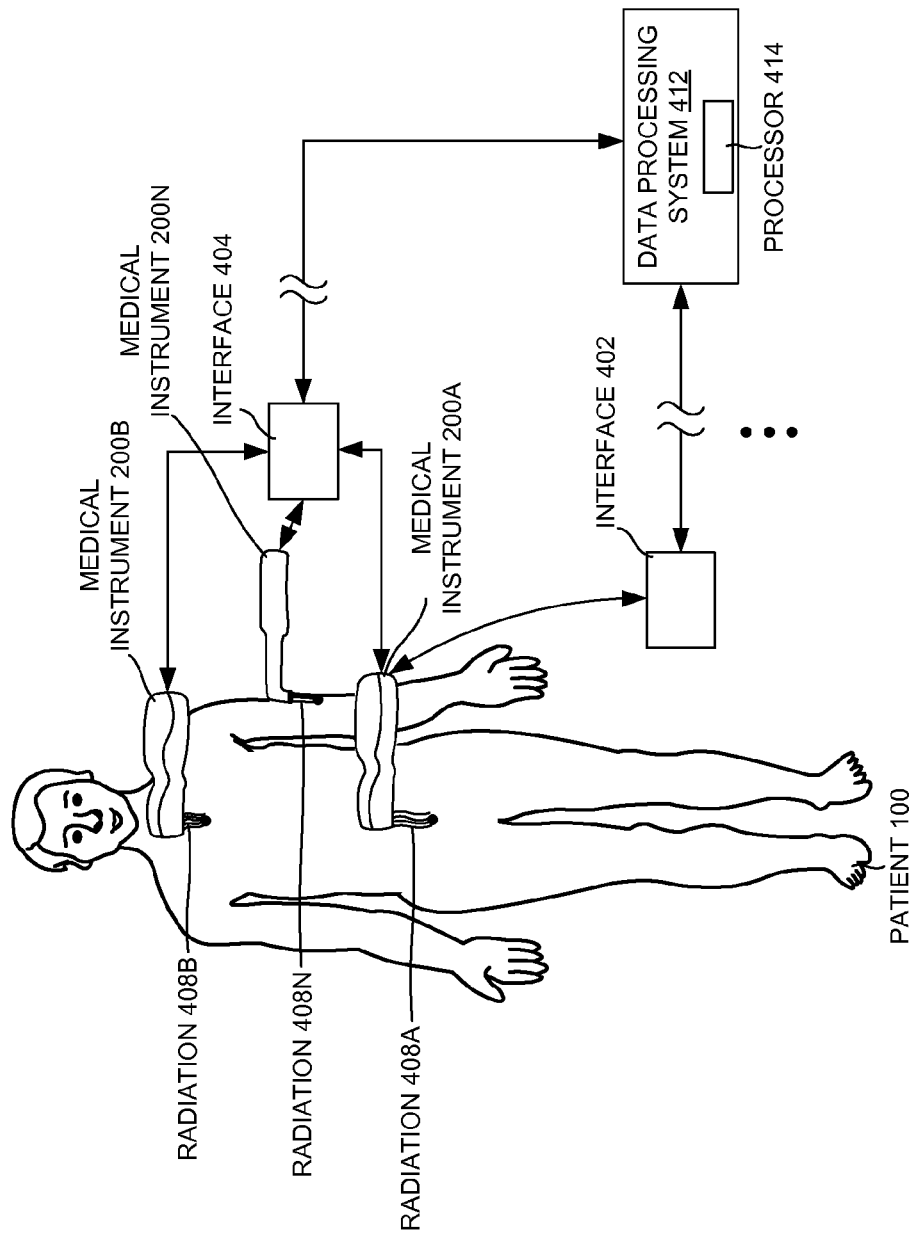
FIG. 4 illustrates a system view that illustrates medical instruments being communicatively coupled and coordinated through a data processing system for treatment of the patient, according to an example embodiment.

FIG. 4 is a system view that illustrates medical instruments 200A-N being communicatively coupled and coordinated through a data processing system 412 for treatment of the patient 100, according to an example embodiment. In particular, FIG. 4 illustrates the medical instruments 200A-N, interfaces 402-404, radiations 408A-N, the data processing system 412, a processor 414, and the patient 100, according to one embodiment.

In one or more embodiments, the medical instruments 200A-N may/may not be coupled to the data processing system 412 during treatment. In one or more embodiments, the medical instruments 200A-N described herein may be portable and hand-held devices. The medical instruments 200A-N may be communicatively coupled to each other and to the data processing system 412 through the interface(s) 402-404. The interface(s) 402-404 may serve as a communication link between the medical instruments 200A-N. In one or more embodiments, there may be any number of interfaces to enable coupling of medical instruments 200A-N. The aforementioned data processing system 412 may be a computing device (e.g., computer) that includes the processor 414. In one or more embodiments, the data processing system 412 may be used for communicating mode information to the medical instruments 200A-N through the interfaces 402-404.

In one or more embodiments, the medical instruments 200A-N coupled to each other through the interfaces 402-404 may generate the radiations 408A-N individually or in coordination. In one or more embodiments, the medical instruments 200A-N may also generate the radiations 408A-N independently. In one or more embodiments, the radiation 408A-N (e.g., soliton waves) may be generated from the laser-light generated by the laser diodes of the medical instruments 200A-N. In one or more embodiments, the radiations 408A-N may be generated in combination and coordination or individually. In another embodiment, an algorithm that coordinates the delivery of laser-light may be controlled by the medical instruments 200A-N. The algorithm may be designed based on the requirement of a medical procedure. It may be noted that the delivery of the radiations is possible even without coordination.

In an example embodiment, each of the medical instruments 200A-N may generate the radiations 408A-N at preconfigured modes. In one or more embodiments, each of the medical instruments 200A-N may be configured individually to generate the radiations 408A-N at specified frequencies. In one or more embodiments, medical instruments 200A-N may be communicatively coupled to the data processing system 412 to communicate new modes to the medical instruments 200A-N. The data processing system 412 may communicate new modes to the medical instruments 200A-N.

There may be a variety of operational modes for operating the medical instruments 200A-N. The operational modes may be based on a suggested form of a treatment. In one or more embodiments, the medical instruments 200A-N may coordinate among each other synchronously, asynchronously, or in a pattern to provide laser therapy. The radiations 408A-N generated may be delivered on biological mediums (e.g., application points in a human body) based on a procedure of medical treatments. In another embodiment, the medical instrument 200A-N may be used by a patient for treatment.

In an example embodiment, the radiations 408A-N may be generated by canceling a nonlinear effect and a dispersive effect in a region between an emitting region of the medical instrument 200A-N and the biological medium. The dispersive effect may be a dispersion relationship (e.g., variation of wave propagation with wavelength or frequency of a wave) between a frequency and a speed of the soliton wave. In one or more embodiments, the medical instruments 200A-N may include primary device and probe devices. The primary device (e.g., the medical instrument 200A) is explained in FIG. 5. The medical instrument 200C may be explained in detail in FIG. 11.

In the example embodiment, FIG. 4 illustrates treatment being provided to hypertension/high blood pressure by applying radiation 408A-N on the application points $300_{1-N}$ for a specified amount of time that may control the symptoms of high blood pressure/hypertension. In one or more embodiments, the radiation 408A-N may be provided for an approximate time of one minute. FIG. 4 illustrates radiation being provided on the application points as illustrated in FIG. 2.

Figure 5:
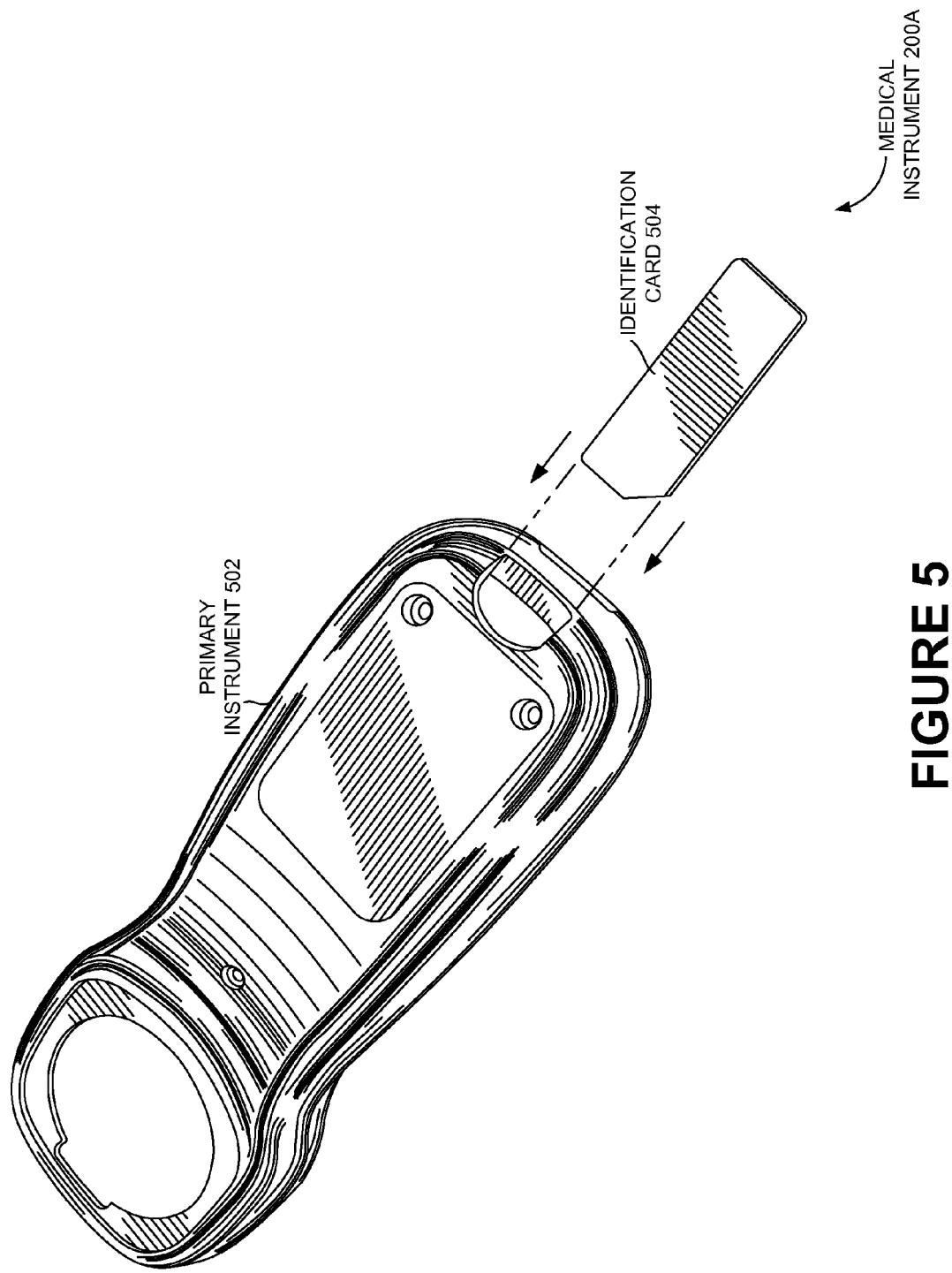
FIG. 5 illustrates a schematic view of a primary instrument, according to one embodiment.

FIG. 5 is a schematic view of a primary instrument 502, according to one embodiment. In particular, FIG. 5 illustrates the primary instrument 502 and an identification card 504, according to one embodiment. In one or more embodiments, the identification card 504 may be used as a mode card, where the modes can be stored on the medical instrument 200A. The identification card 504 may activate the modes stored on the medical instrument 200A.

In an example embodiment, the medical instrument 200A may be the primary instrument 502. The primary instrument 502 as described herein may include the identification card 504. In one or more embodiments, the identification card 504 of the medical instrument 200A may be used for selecting an operational mode of the medical instrument 200A. The identification card 504 coupled to the primary instrument 502 may be removable by a user of the medical instrument 200A. The operational modes may be associated with a suggested form of a medical treatment. There may be a variety of operational modes for a treating of a particular ailment. A patient 100 may choose a best mode of treatment based on his condition of the disease. The patient 100 may choose a best operational mode for the treatment using the medical instrument 200A.

In one or more embodiments, the operational modes may be stored on medical instrument 200A, and the best operational mode may be activated by the identification card 504. The identification card 504 may be programmed using an appropriate device. Furthermore, the identification card 504 may be reprogrammed based on a prescription associated with the therapeutic condition of the patient 100. In one or more embodiments, the patient 100 may decide on a custom mode for providing an additional treatment by the medical instrument. In one or more embodiments, the custom mode of operation of the medical instruments 200A-N may be generated and/or determined based on a response of the user. The custom mode may be suggested by the instrument maker and/or may be programmed into the identification card 504. The identification card 504 may be communicatively coupled to the primary instrument 502 through a port designated for that purpose. The primary instrument 502 may then generate a radiation based on the mode that is loaded from the identification card 504. In one or more embodiments, a name associated with the custom mode of operation may be created and the configuration associated with the custom mode may be stored in the data processing system 412 for future treatments.

In alternate embodiments, the identification card 504 may be made specific to one therapeutic condition (e.g., hypertension/blood pressure). In one or more embodiments, the operational modes of the medical instruments 200A-N may be provided from the data processing system 412 thereof. In one or more embodiments, the custom mode may be shared with the other medical instruments based on a set of rules and preferences of the user and/or the doctor 102. In one or more embodiments, the custom mode may be shared by communicating the custom mode to the data processing system 412 and applying the custom mode to the other medical instruments through the data processing system 412.

In one or more embodiments, the medical instrument 200A may be used for treatment in general conditions. Also, in one or more embodiments, the medical instrument 200B described herein may be substantially similar to the medical instrument 200A. In one or more embodiments, where there is a requirement of directed, high-power dosage in a narrow region of a biological medium, the second medical instrument 200C, for example may be a probe device may be used. The probe device may be explained in detail in FIG. 11. The primary device or the medical instrument 200A may be explained in detail in FIG. 10.

Figure 6:
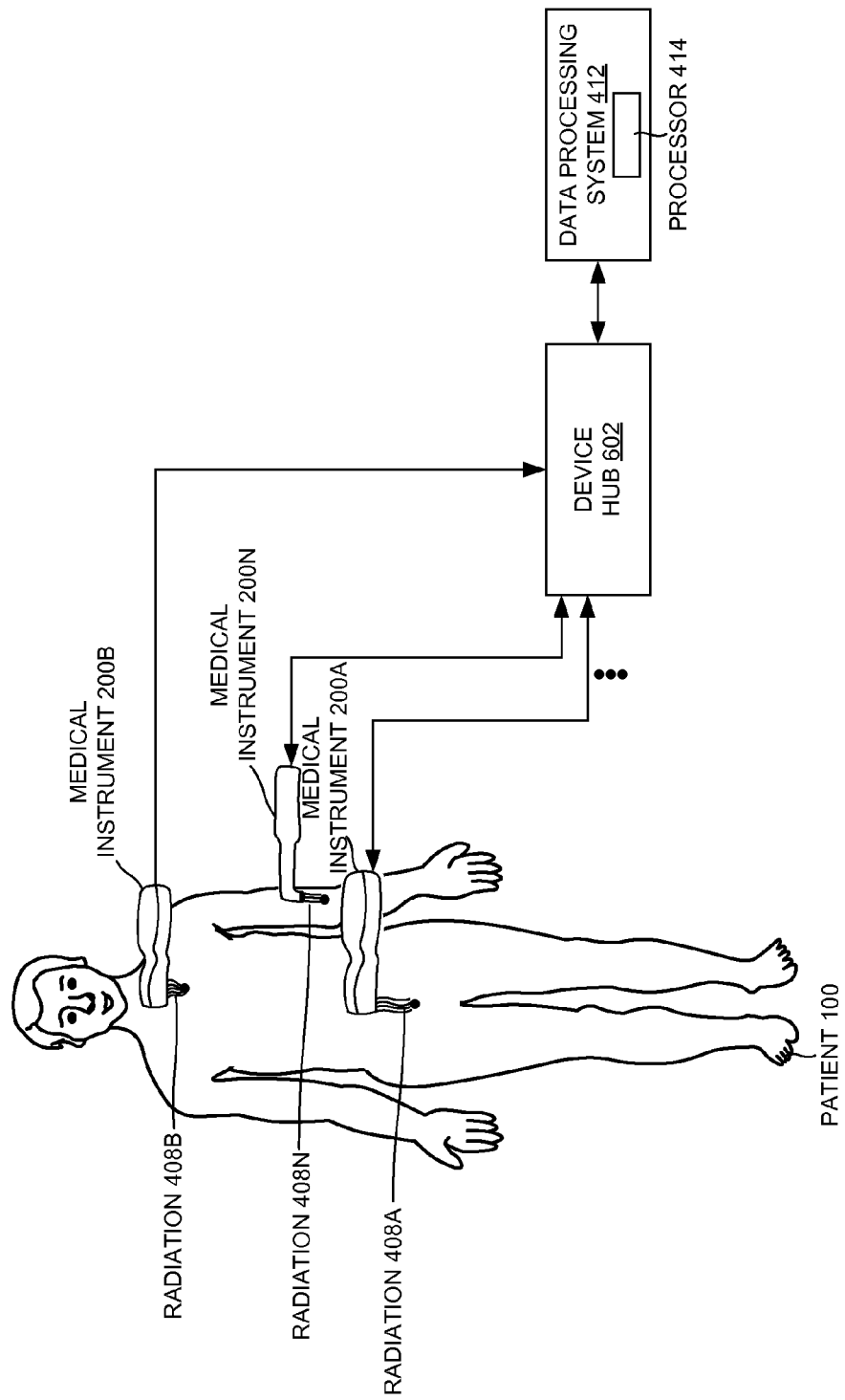
FIG. 6 illustrates an alternative system view comprising the medical instruments that are communicatively coupled and coordinated through a data processing system for treatment of the patient, according to another embodiment.

FIG. 6 is an alternative system comprising the medical instruments 200A-N that are communicatively coupled and coordinated through the data processing system 412 for treatment of a patient 100, according to another embodiment. In particular, FIG. 6 illustrates the patient 100, the medical instruments 200A-N, a device hub 602, the radiations 408A-N, the data processing system 412, and the processor 414, according to an alternate embodiment.

FIG. 6 provides an alternative embodiment to the system illustrated in FIG. 4. In an embodiment, the medical instruments 200A-N may be communicatively coupled to the data processing system 412 through the device hub 602. The device hub 602 may be a device that is used to connect the medical instruments 200A-N to the data processing system 412. In an example embodiment, the device hub 602 may serve as a bridge between the medical instruments 200A-N and the data processing system 412. Each of the medical instrument 200A-N may be connected to the device hub 602. The processor 414 in the data processing system 412 may provide modes of treatment to the medical instruments 200A-N through the device hub 602. In one or more embodiments, the system as illustrated in the FIG. 6 may substantially same as the system described in FIG. 4.

Figure 7:
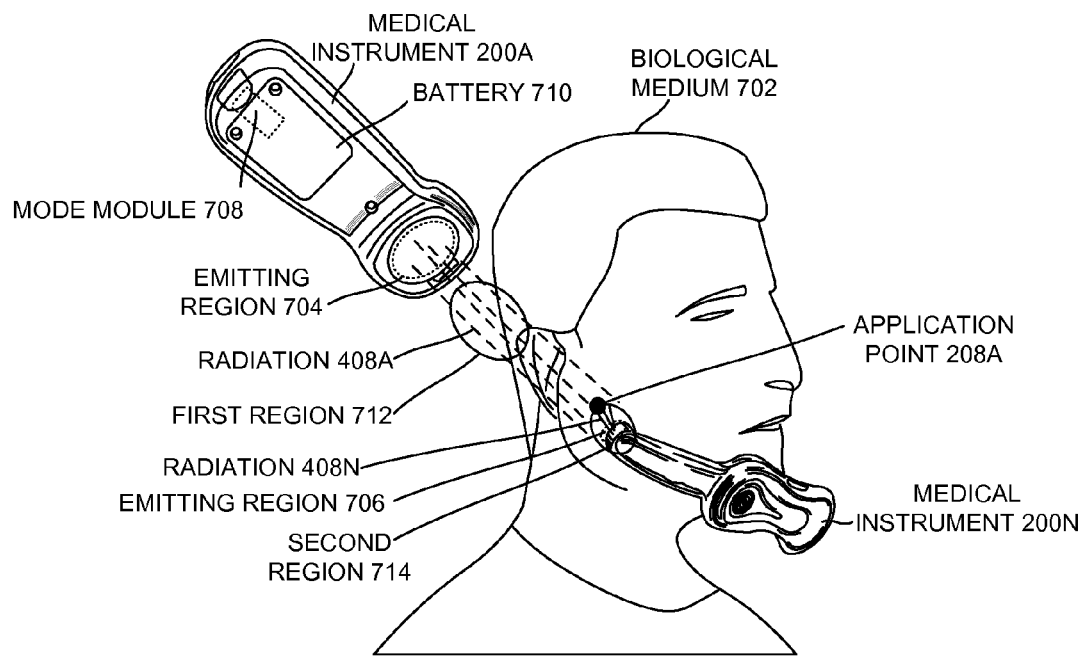
FIG. 7 illustrates a use of the medical instruments used for providing treatment to a biological medium, according to one embodiment.

FIG. 7 is a schematic view illustrating a use of the medical instruments 200A-N for providing treatment to a biological medium 702, according to one embodiment. FIG. 7 illustrates the biological medium 702, an emitting region 704, an emitting region 706, a mode module 708 and a battery 710. In one or more embodiments, the biological medium 702 described herein may be a part of a patient's body that includes an application point. In alternate embodiments, the biological medium 702 may be an animal or bird or any other concerned life form affected by the disease. The medical instruments 200A-N described herein may be used on the biological medium 702 individually or in coordination to provide radiation to the affected areas. In an example embodiment, the radiation 408A may be generated by canceling a nonlinear effect and a dispersive effect in a first region 712 between an emitting region of the medical instrument 200A and the biological medium. In an example embodiment, the radiation 408N may be generated by canceling a nonlinear effect and a dispersive effect in a second region 714 between an emitting region of the medical instrument 200N and the biological medium. The dispersive effect may be a dispersion relationship (e.g., variation of wave propagation with wavelength or frequency of a wave) between a frequency and a speed of the soliton wave. The medical instrument 200A may be powered using a battery 710. In an alternate embodiment, the medical instrument 200A may also be powered through external sources (e.g., through a power cord). In an example embodiment, the battery 710 may be a lithium-ion rechargeable battery to power the medical instruments 200A.

The medical instrument 200A-N described herein may be authenticated based on an identifier associated with the medical instruments 200A-N using the processor 414. In one or more embodiments, the authentication of the user of the medical instruments 200A-N may be based on a password using the processor 414. In one or more embodiments, a set of rules associated with the medical instrument(s) may be provided based on the identifier and the user.

Figure 17A:
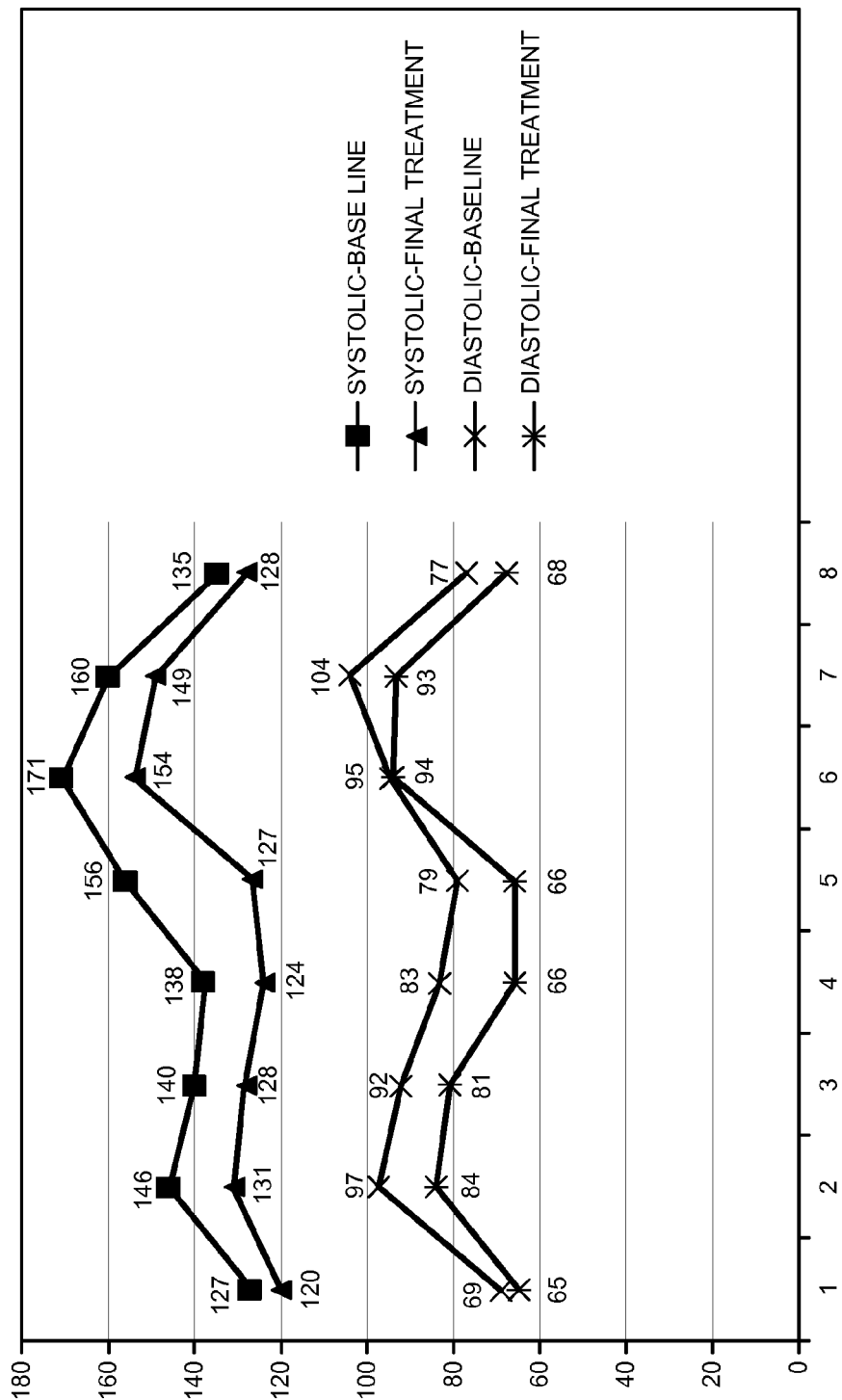
FIG. 17A illustrates hypertension/blood pressure study results for 8 patients.

FIG. 17A illustrates a hypertension/high blood pressure study results for 8 individuals suffering from hypertension/high blood pressure. Each co-ordinate illustrated on x-axis may represent a patient for which the results may be taken and y-axis may represent the blood pressure. A systolic base line may illustrate which may represent the systolic pressure level of the patients prior to the treatment. A systolic final treatment line may represent the systolic pressure level of the patients after the completion of the treatment. The systolic final treatment line illustrates the reduction in the systolic component of the blood pressure of the patients as compared to the systolic baseline. Similarly, a diastolic final treatment line also may illustrate a reduction in the diastolic component of the blood pressure of the patients as compared to a diastolic-baseline (e.g., which indicated initial diastolic blood pressure). Significant reduction in the blood pressure levels may be observed in the patients after the completion of the treatment.

FIG. 17B shows clinical trials result in reduction of blood pressure levels in patients suffering from hypertension/high blood pressure with various treatment periods ranging from 45-60 days. The FIG. 17B provides information of blood pressure of individuals as illustrated in FIG. 17A. The treatment with a laser based medical instrument was provided along with suggested oral medications. None of the medications were discontinued during the treatment period. Significant percentage drop in blood pressure levels were observed after set period of treatment days. The observations and percentage in reduction/increase is illustrated in FIG. 17B.

Figure 8:
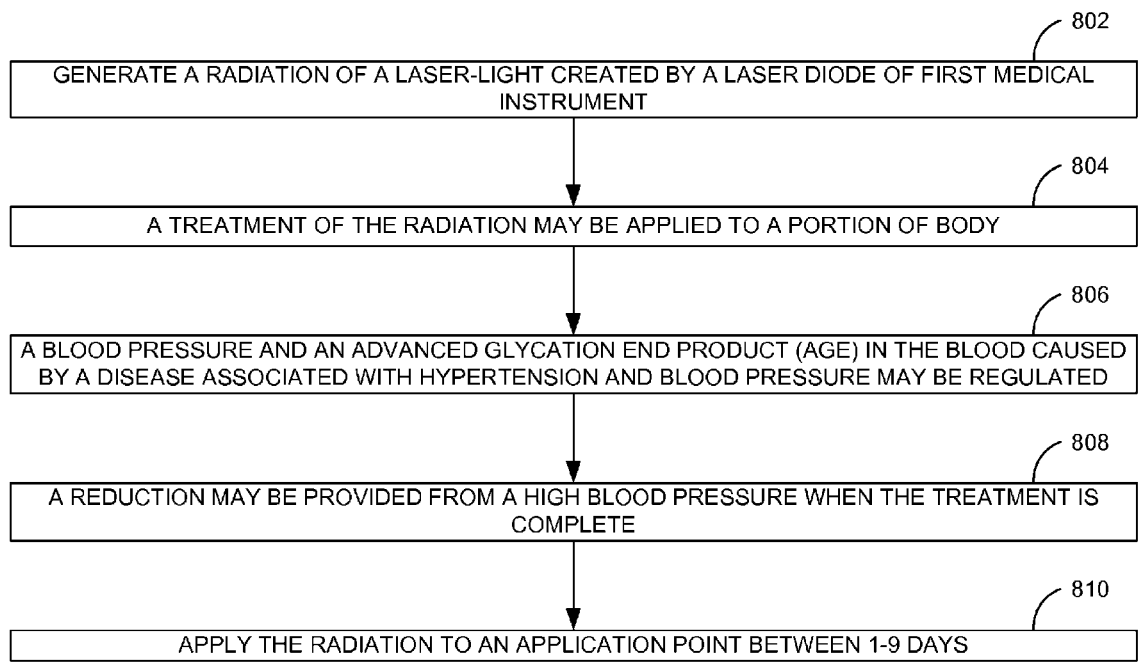
FIG. 8 is a process flow illustrating a treatment being provided through the medical instruments, according to one or more embodiments.

FIG. 8 is a process flow illustrating a treatment being provided through a medical instruments 200A-N, according to one or more embodiments. In operation 802, a radiation 204 of a laser-light created by a laser-diode 202 of a first medical instrument may be generated. In operation 804, a treatment of the radiation may be applied to a portion of a body. In one or more embodiments, a treatment of the radiation 204 generated by the medical instruments 200A-N may be applied on the application points $300_{1-N}$ of the patient 100 suffering from hypertension/high blood pressure.

In operation 806, a blood pressure and/or an AGE product in the blood caused by a disease associated with hypertension and blood pressure may be regulated. In operation 808, a reduction may be provided from the high blood pressure when the treatment is complete. In one or more embodiments, in operation 810, the radiation may be applied to an application point between 1-9 days as illustrated in FIG. 16.

Figure 9:
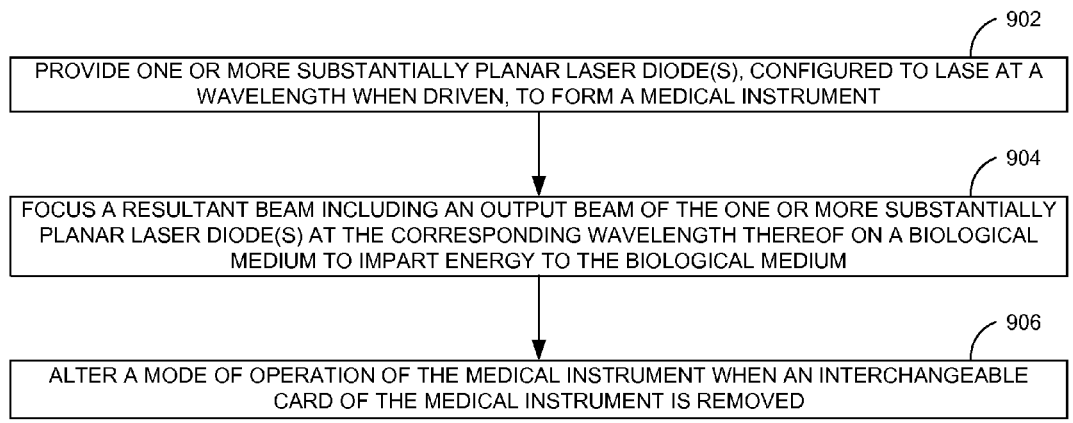
FIG. 9 is a process flow detailing the operations involved in a method of laser therapy, according to one or more embodiments.

FIG. 9 is a process flow detailing the operations involved in a method of laser therapy, according to one or more embodiments. In operation 902, one or more substantially planar laser diode(s), each configured to lase at a wavelength when driven, may be provided to form a medical instrument. In one or more embodiments, a number of substantially planar laser diodes may be arranged in a pre-determined configuration to form a substantially planar laser diode array. In one or more embodiments, the substantial planarity, along with a symmetrical pre-determined configuration, may provide for a symmetrical combination of the output beams from the number of substantially planar laser diodes to form a highly directed resultant beam.

In one or more embodiments, the soliton waves may be generated from the one or more substantially planar laser diode(s). In one or more embodiments, end minors of the one or more substantially planar laser diode(s) may be replaced with anti-reflection coatings, and when the one or more substantially planar laser diode(s) are driven, the optical field evolution in the laser diode(s) may be modeled by using two coupled differential equations (example Equations 1 and 2) as:

$$\frac{\partial \varphi}{\partial z} = i\frac{\partial^2 \varphi}{2\partial x^2} + (-ihN + (N-1) - \alpha)\varphi, \quad (1)$$

and $$D\frac{\partial^2 N}{\partial x^2} = -\pi + N + BN^2 + CN^2 + (N-1)|\varphi|^2, \quad (2)$$

where $\varphi$ may be the optical field solution, $i=\sqrt{-1}$, x and z the spatial coordinates, the Henry factor, $\alpha$ the internal loss, N the normalized carrier density $$(N = \frac{N'}{N'_{tr}}, N',$$

being the carrier density, and $N'_{tr}$ being the transparency carrier density), D the carrier diffusion coefficient, $\pi$ the current pumping coefficient, B the spontaneous recombination coefficient, and C the Auger recombination rate. Here, a linear dependence of the induced refractive index and gain on the carrier density N' may be assumed.

In one or more embodiments, neglecting carrier diffusion in the z direction, and assuming small diffusion, B=0, and C=0, a generalized complex Ginzburg-Landau equation may be obtained from Equations 1 and 2 as example Equation 3:

$$\frac{\partial \varphi}{\partial z} = i\left(\frac{1}{2} - i\beta\right)\frac{\partial^2 \varphi}{\partial x^2} + \left(\frac{\pi - 1}{1 + |\varphi|^2}(-ih + 1) - ih\right)\varphi - \alpha\varphi, \quad (3)$$

where β may account for the transverse carrier diffusion.

In one or more embodiments, soliton wave solutions of the form $\phi(x)e^{i\lambda z}$ may be numerically obtained. In one or more embodiments, depending on the arrangement of the number of substantially planar laser diodes, constructive interference of the outputs of the number of substantially planar laser diodes may lead to a resultant soliton wave of high amplitude. In one or more embodiments, the resultant soliton wave output may have an amplitude several times higher than a non-soliton wave resultant beam.

In operation 904, the resultant beam may be directed on a biological medium to impart energy to the biological medium (e.g., humans). In one or more embodiments, the resultant beam may be directed on a portion of the human body to treat conditions such as hypertension/blood pressure. In one or more embodiments, in operation 906, a mode of operation of the medical instrument may be altered upon removal of the identification card 504 of the medical instrument. In one or more embodiments, the identification card 504 may be therapeutic condition specific (e.g., hypertension/blood pressure), and the insertion of a new identification card into the medical instrument may result in the medical instrument operating solely in modes of operation specific to the therapeutic condition. In other words, access to mode information is restricted to modes of operation specific to the therapeutic condition.

In one or more embodiments, altering the mode of operation of the medical instrument upon removal of the identification card, as in operation 906, may involve substituting an identification card with another identification card. In one or more embodiments, one identification card may be specific to one therapeutic condition (e.g., hypertension/blood pressure), and the other identification card may be specific to another therapeutic condition (e.g., arthritis).

In one or more embodiments, a mode of operation may include one or more segments, where a segment includes a time of pulsation of the one or more substantially planar laser diode(s) and a frequency of pulsation of the one or more substantially planar laser diode(s).

Figure 10:
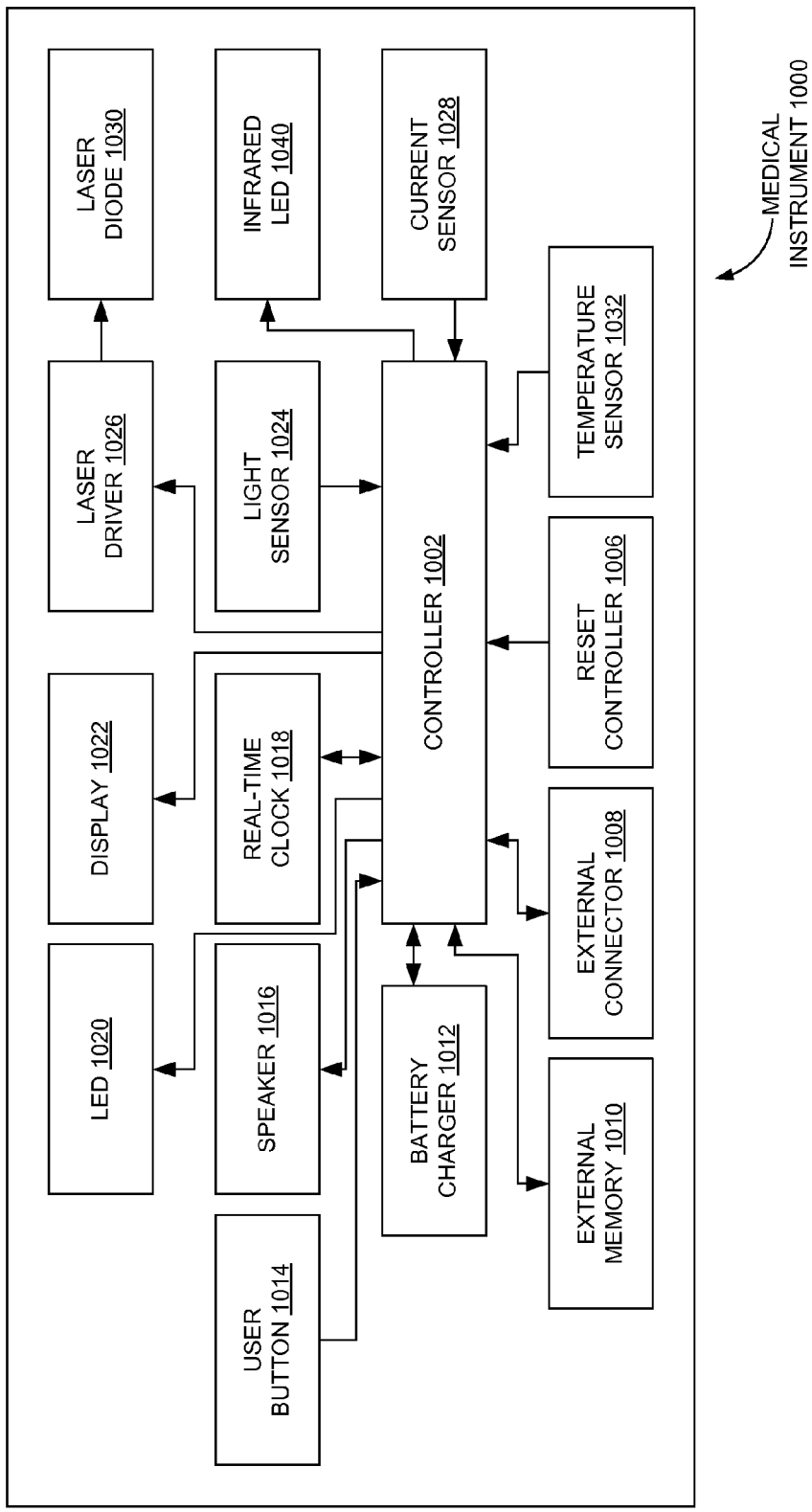
FIG. 10 is a schematic view of a medical instrument, according to one or more embodiments.

FIG. 10 is a schematic view of a medical instrument 1000, according to one or more embodiments. The medical instrument 1000 may in specific describe a schematic representation of the medical instrument 200A-B and the primary instrument 502. In one or more embodiments, the medical instrument 1000 may include a controller 1002 to control operations fundamental to the working of the medical instrument 1000. In one or more embodiments, the controller 1002 may include a permanent memory (e.g., flash memory) to store firmware associated with controlling the medical instrument 1000. In one or more embodiments, modes of operation may internally be set in the firmware. In one or more embodiments, the controller 1002 is interfaced with a battery charger 1012 to charge a battery (e.g., internal battery) of the medical instrument 1000. In one or more embodiments, the battery charging capability may be provided through an external connector 1008 that may serve purposes not limited to battery charging.

In one or more embodiments, the external connector 1008 may be a multi-pin and multi-use external connector that may also be used to program the internal controller of the medical instrument 1000 (e.g., controller 1002), to calibrate constituent laser diodes 1030, to couple other external compatible devices (e.g. another medical instrument 1000, a probe version of the medical instrument 1000, a computer device, a personal digital assistant (PDA)) and/or to perform diagnostics of the medical instrument 1000.

In one embodiment, the medical instrument 1000 may be powered by a lithium-ion rechargeable battery placed in an inside thereof. Here, the battery charger may plug into the medical instrument 1000 through the external connector 1008, and may closely monitor charge current as well as maximum allowed voltage. In one or more embodiments, the battery may be supplied with a safety circuitry to prevent over-charging/over-discharging of the battery. In one or more embodiments, constituent components of the medical instrument 1000 may be powered during charging of the battery, but user interaction with the medical instrument 1000 may not be possible.

In one or more embodiments, the controller 1002 may be interfaced with an external memory 1010 to enable the medical instrument 1000 to record data indicating a diagnostic requirement of the medical instrument 1000. In one or more embodiments, the recorded data may be useful in enabling servicing of the medical instrument 1000. For example, corrective diagnostics may be performed on the medical instrument 1000 by service personnel following a return of the medical instrument 1000 by a user. In one or more embodiments, the external memory 1010 may be a non-volatile memory such as an Electrically Erasable Programmable Read-Only Memory (EEPROM).

In one or more embodiments, the medical instrument 1000 may be provided with a user button 1014 (shown in FIG. 10 as turning on the controller 1002) to simplify operations thereof. In one embodiment, the user button 1014 may serve as both the power ON/OFF button and the mode selection button.

In one or more embodiments, the medical instrument 1000 may be provided with a speaker 1016 (shown in FIG. 10 as being controlled by the controller 1002) to generate audible alerts as well as indicate the pressing of the user button 1014. In one or more embodiments, the audible alerts may indicate one or more of an operational status of the medical instrument 1000, a beginning of a mode of operation, a beginning of a segment, an end of a mode of operation, and an end of the segment. In one or embodiments, all audible alerts may be muted by the user during use of the medical instrument 1000.

In one or more embodiments, to enhance serviceability of the medical instrument 1000, a real-time clock 1018 (shown in FIG. 10 as being interfaced with the controller 1002) may be implemented in the medical instrument 1000. In one or more embodiments, data recorded in the external memory 1010 may always be tagged with a current date and time at the time of recording. In one or more embodiments, this may enable a history of use of the medical instrument 1000 to be tracked. For example, when the medical instrument 1000 is returned to the service personnel, the service personnel may be better equipped to understand problems associated with the functioning of the medical instrument 1000.

In one or more embodiments, the medical instrument 1000 may be equipped with one or more LEDs 1020 and a display 1022 (e.g., seven segment display) that serve as user indicators. In FIG. 10, the LEDs 1020 and the display 1022 are shown as being controlled by the controller 1002. In one embodiment, an operational state of the medical instrument 1000 may be indicated with an LED emitting green light that may turn red during a power down. Here, another LED may be provided to indicate battery state and battery charging. For example, if the light emitted by this LED turns yellow during normal operation, it may be indicative of a low power level of the battery. The battery may then need to be charged. The LED may emit red light in a blinking state until charging may be complete, following which the LED may continue to emit green light. In one or more embodiments, the display 1022 may indicate modes that are loaded onto the medical instrument 1000, and, in one embodiment, the modes may be indicated on the display as 0-9. Here, the user may select a mode using the mode selection feature of the user button 1014.

In one or more embodiments, one of the purposes of the controller 1002 may be to control the laser diodes 1030 through laser drivers 1026 thereof. In one or more embodiments, the controller 1002 may control the power level of the laser diodes 1030, and also the flashing of the laser diodes 1030. In addition, in one or more embodiments, the controller 1002 may monitor a light sensor 1024 that measures an ambient light outside the medical instrument 1000. This measurement may be used to control the light intensity of the user indicator LEDs 1020.

In one or more embodiments, the controller 1002 may have the ability to sense the operating current of each laser diode 1030 (see the current sensor 1028 in FIG. 10), which may be used to deactivate laser diodes 1030 that may have failed. In one or more embodiments, this may ensure safety of operation of the medical instrument 1000. In one or more embodiments, current may also be sensed during calibration of the medical instrument 1000 to ensure proper operation of the laser diodes 1030. In one or more embodiments, a power management circuitry of the laser diodes 1030 may be controlled by the controller 1002. In one or more embodiments, infrared light may also be emitted from the infrared LEDs 1040.

In one or more embodiments, the medical instrument 1000 may also include a number of infrared LEDs 1040 (shown as being controlled in FIG. 10 by the controller 1002) to emit infrared light during a duration of a mode of operation. In one or more embodiments, the infrared LEDs 1040 may operate in conjunction with one or more of the visible LEDs 1020.

In one or more embodiments, the controller 1002 may monitor a temperature sensor 1032 to obtain accurate values of the temperatures of the laser diodes 1030. In one or more embodiments, variations of temperature of the laser diodes 1030 may also be tracked.

In one or more embodiments, the medical instrument 1000 may include a reset controller 1006 to monitor a reset button. For example, when a user depresses the reset button and holds the reset button for, say, 5 seconds, the reset controller 1006 may send a reset signal to the controller 1002 to reset the medical instrument 1000. Here, 5 seconds is the threshold time period, and if a user presses the reset button for a time period exceeding the threshold time period, the medical instrument 1000 may be reset.

In one or more embodiments, when the medical instrument 1000 is turned ON and is in an idle state, an LED 1020 indicating power may emit green light. In one or more embodiments, a shut off timer may be started internally to turn the medical instrument 1000 off in case of inactivity (e.g., no further pressing of buttons) for a time period exceeding another threshold time period.

In one or more embodiments, the medical instrument 1000 may be pre-programmed (e.g., by the manufacturer) with several operational modes. In one or more embodiments, the modes may be pre-programmed with the duration of treatment for a therapeutic condition, and the specific frequencies the medical instrument 1000 may be operating at.

Figure 11:
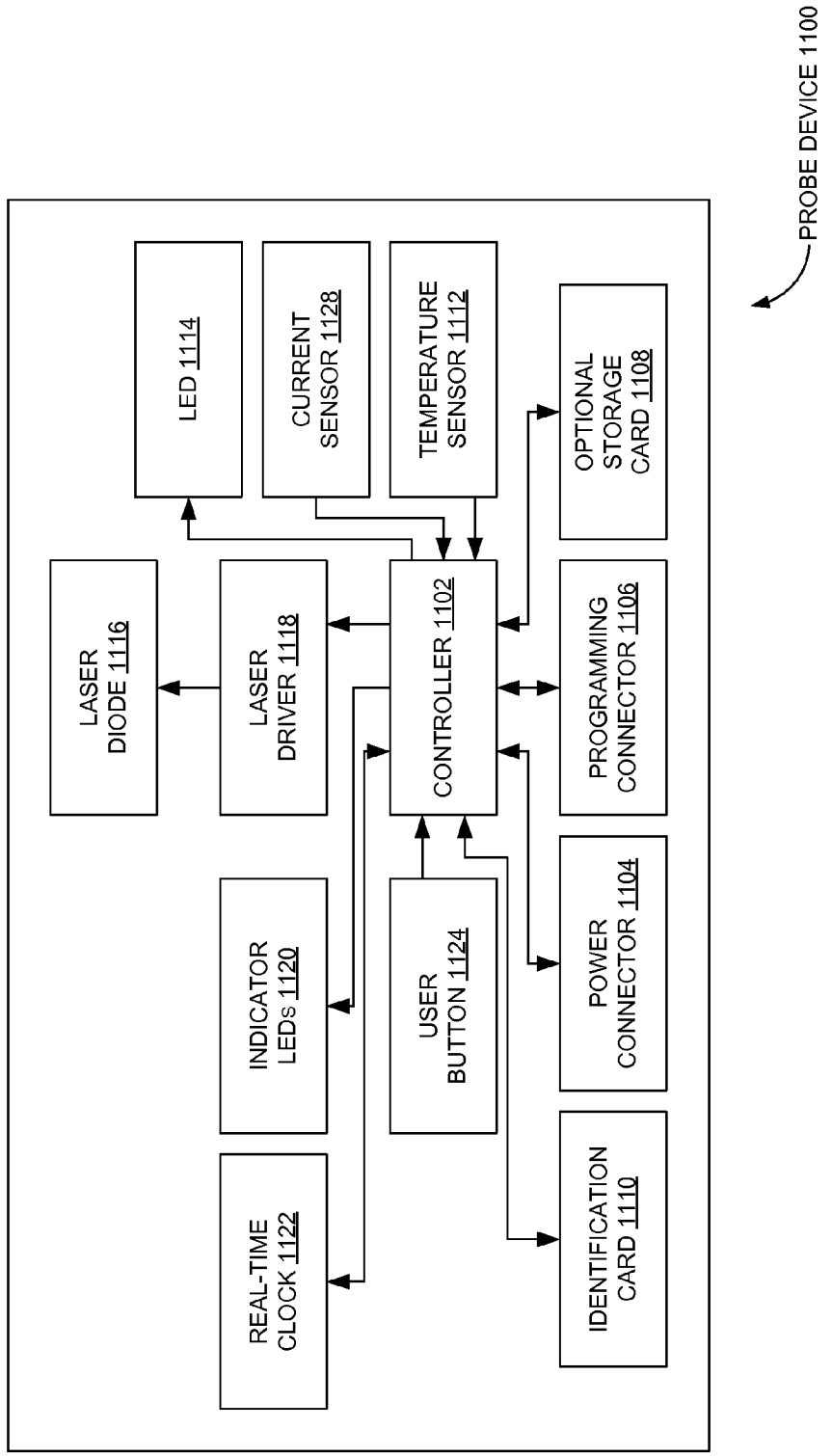
FIG. 11 is a schematic view of a probe device, according to one or more embodiments.

In one or more embodiments, where there is a requirement of directed, high-power dosage in a narrow region of a biological medium, the second medical instrument 200C, for example, may be a probe device (as illustrated in FIG. 11).

FIG. 11 is a schematic view of a probe device 1100, according to one or more embodiments. The probe device 1100 may be substantially similar to, or the same as, the medical instrument 200C. In one or more embodiments, the probe device 1100 may include a controller 1102 to control all components of the probe device 1100. In one or more embodiments, an operating program of the controller 1102 may be user-upgraded using an optional storage card 1108. In one or more embodiments, the optional storage card 1108 may be a flash card from which different programs may be read.

In one or more embodiments, the probe device 1100 includes a power connector 1104 through which a battery of the probe device 1100 may be charged. In one or more embodiments, the medical instrument 200A may be used to power the probe device 1100 through the power connector 1104. In one or more embodiments, the probe device 1100 may include an identification card 1110. The identification card 1110 may include information regarding types of treatment modes to be activated. The information on the identification card 1110 may be read by controller 1102.

In one or more embodiments, the probe device 1100 may include a programming connector 1106 through which a programming/calibration interface may be provided. In one or more embodiments, the probe device 1100 may be calibrated by a manufacturer and/or serviced by service personnel through the programming connector 1106. In one or more embodiments, a data processing system 412 may be coupled to the probe device 1100 through the programming connector 1106. In one or more embodiments, the programming connector 1106 may not be available to a user but only available to the manufacturer and/or service personnel.

In one or more embodiments, an integrated laser driver 1118 may control a laser diode 1116 of the probe device 1100. In one or more embodiments, an operating current of the laser diode 1116 and/or a light output of the laser diode 1116 may be monitored to maintain a constant output of the laser diode 1116. In one or more embodiments, the laser diode 1116 may be calibrated during the manufacturing process and/or the laser driver 1118 may be configured to handle a range of laser diodes.

In one or more embodiments, LEDs (1114, 1120) may be provided to indicate an operational state of the probe device 1100. A light from an LED 1114 may also indicate that the optional storage card 1108 is properly inserted and recognized. In another example, a number of LEDs 1120 may indicate modes selected and/or progress during boot-up. In one or more embodiments, a separate LED 1114 may indicate activity of the laser diode 1116.

In one or more embodiments, in order for corrective diagnostics to be performed by service personnel and/or operating statistics to be obtained by the manufacturer, a real-time clock 1122 may be provided in the probe device 1100. In one or more embodiments, the real-time clock 1122 may be programmed during manufacturing. In one embodiment, power to the real-time clock 1122 may be supplied by a coin cell battery of the probe device 1100.

In one or more embodiments, the controller 1102 may monitor the current of the laser diode 1116 during operation of the laser diode 1116 through a current sensor 1128. In one embodiment, the current data may be used in the calibration of the probe device 1100.

In one or more embodiments, a temperature sensor 1112 may be provided in the probe device 1100 to monitor a temperature of the laser diode 1116 in order to ensure safety of operation of the probe device 1100.

In one or more embodiments, when the probe device 1100 is powered up, green light may be emitted from an LED 1120.

In one embodiment, when the optional storage card 1108 is not present, the green LED 1120 may start to blink to indicate the need to insert the optional storage card 1108. In one or more embodiments, upon insertion of the identification card 1110 and checking for updates residing in the identification card 1110, modes of operation may be downloaded into the probe device 1100. In one or more embodiments, modes of operation present on the identification card 1110 may be loaded.

In one or more embodiments, user selection of modes of operation may be accomplished through a user button 1124. In one or more embodiments, the probe device 1100 may be turned on by a user holding the user button 1124 for a time period exceeding a threshold time period of, say, 5 seconds. In one or more embodiments, a warning LED 1114 may be provided to indicate a state where a laser diode 1116 operating at a wavelength outside the visible spectrum may be used. In one or more embodiments, the probe device 1100 may also be turned off by a user depressing the user button 1124 for a time period exceeding another threshold time period. In one or more embodiments, if at any point the identification card 1110 is removed, the laser diode 1116 may be turned off, and the probe device 1100 may return to a boot-up state thereof.

Figure 12:
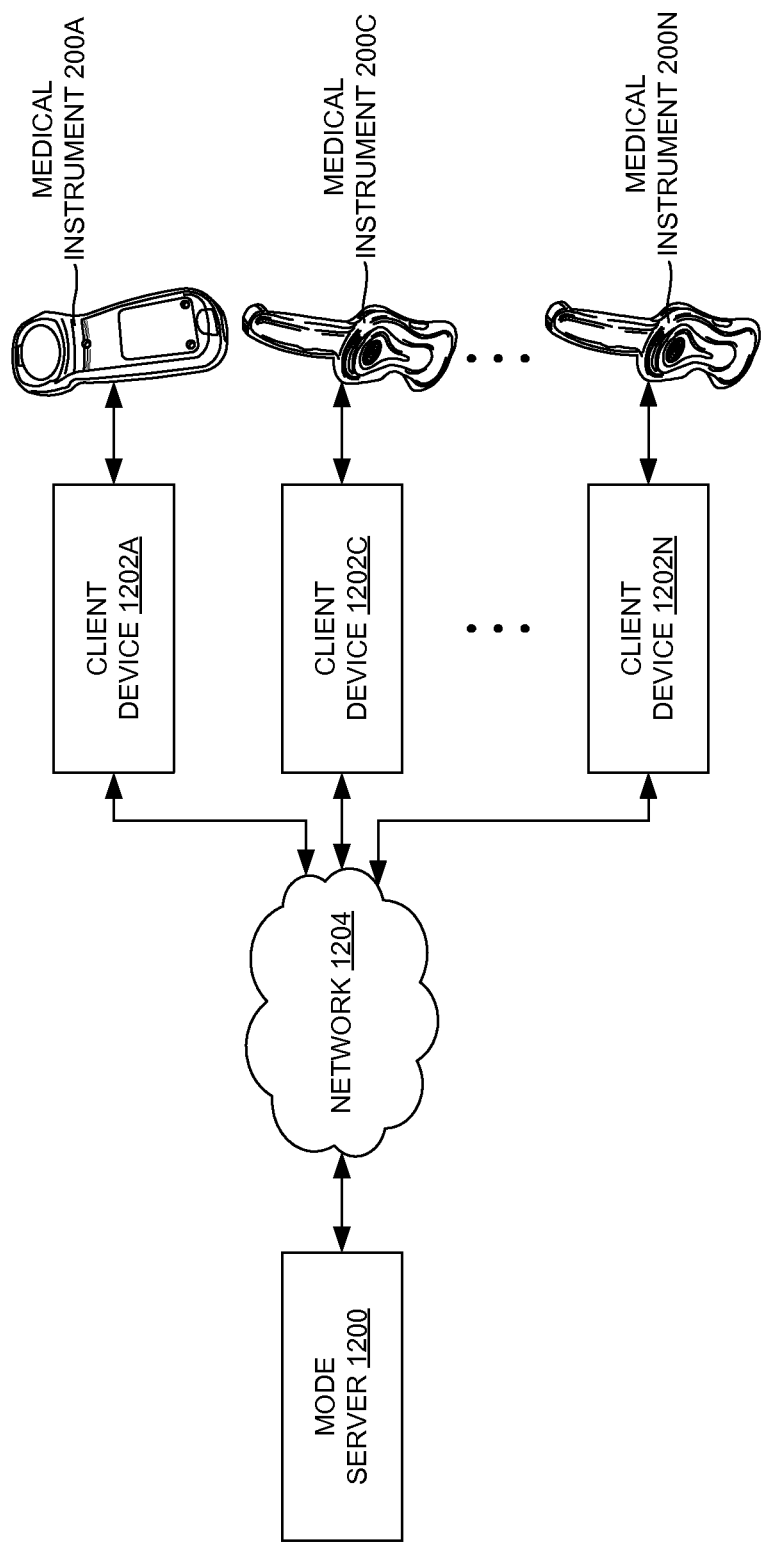
FIG. 12 is a system view illustrating a mode server communicating information associated with a mode to a medical instrument(s) through a client device(s) via a network, according to one or more embodiments.

FIG. 12 is a system view illustrating mode server 1200 communicating information associated with a mode to a medical instrument(s) 200A-B through a client device(s) 1202A-N via a network 1204, according to one or more embodiments. Particularly, FIG. 12 illustrates a mode server 1200, a client device(s) 1202A-N, a network 1204, and the medical instrument(s) 200A-N, according to one or more embodiments. It should be noted that the medical instruments described herein the Figure are substantially similar or the same as illustrated in previous Figures.

The mode server 1200 may provide different modes of operation for the medical instruments 200A-B via the network 1204. The client device 1202A-N may be any computing device (e.g., the data processing system 412) that can interface the medical instrument 200A-N for communicating the mode of operation to the other medical instrument 200A-N. The mode may control the laser diodes and the LED diodes (not shown in figures) to generate a laser wavelength based on the mode. In one or more embodiments, the mode may configure the laser diodes and the LED diodes to generate laser at different wavelengths. In one or more embodiments, the client device 1202A-N may include, but is not limited to, a computer. In one or more embodiments, the client device 1202A-N upon receiving the information may provide an acknowledgment to the mode server via the network 1204. In one or more embodiments, the information associated with the mode may include, but is not limited to, a mode configuration, setting information, and handling instructions. In one or more embodiments, the mode server 1200 may be supported by a custom mode database (not shown in the Figure). The custom mode database may be a central resource for information associated with the modes. In one or more embodiments, a custom mode of operation may be configured into the medical instrument 200A-N and the treatment based on the custom mode may be provided to the user. In one or more embodiments, the custom mode configured by the user may be communicated to the mode server 1200 through the client device 1202A-N via the network 1204.

Figure 13:
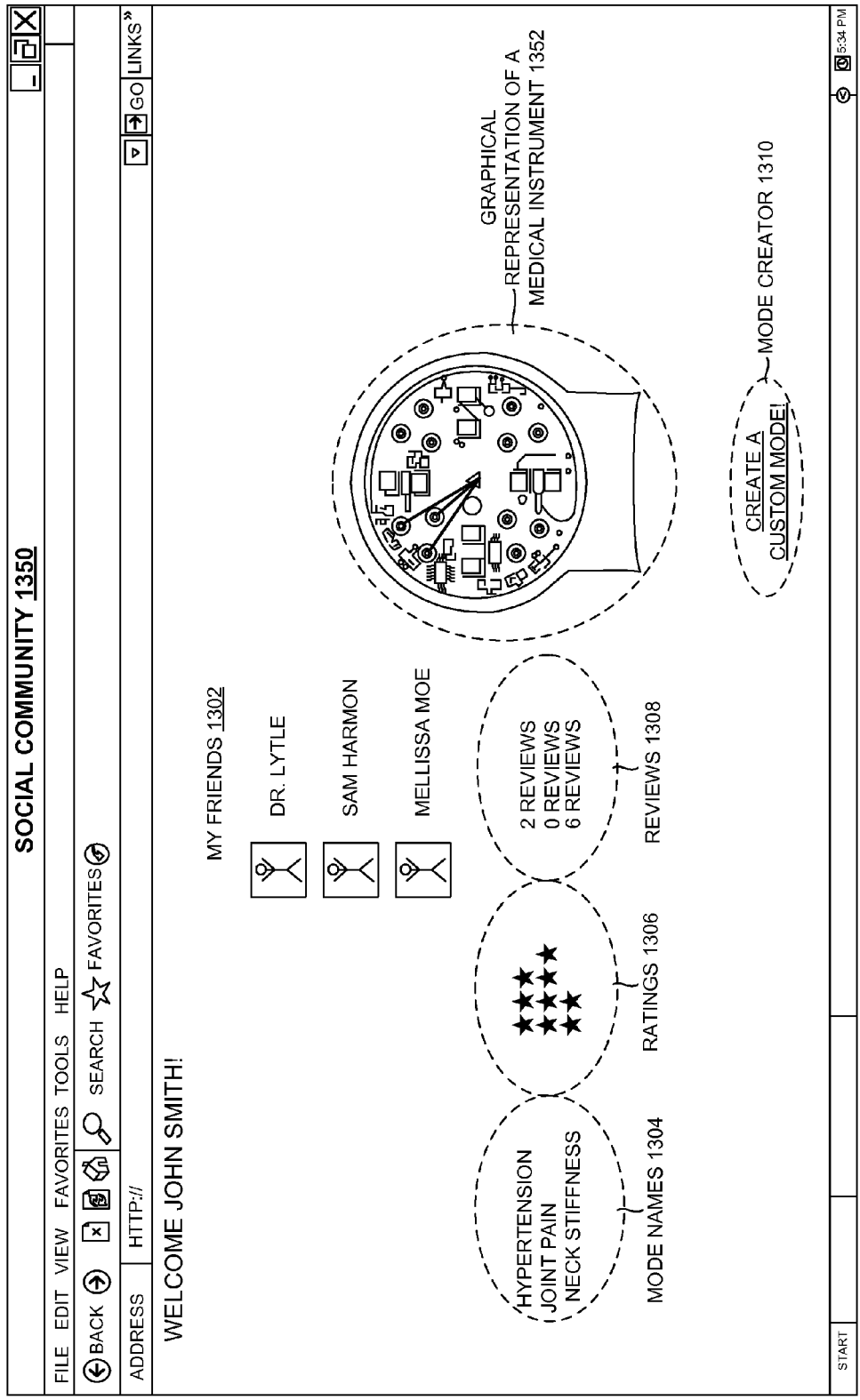
FIG. 13 is a user interface view providing a platform for medical instrument users to interact with other medical instrument users in an online social community environment, according to an example embodiment.

FIG. 13 is a user interface view 1354 providing a platform for medical instrument users to interact with other medical instrument users in an online social community environment 1350, according to an example embodiment. In one or more embodiments, the users of the medical instruments 200A-N may be provided with an online social community environment 1350 (e.g., optional). The medical instrument users may communicate with other medical instrument users, doctors, etc., to share their experiences, provide suggestions, etc. An example embodiment illustrates a user page of the user John Smith. A list of my friends 1302 illustrates a list of friends of the user John Smith, who may be a part of social community 1350. In the example embodiment, the user John Smith may have Dr. Lytle, Sam Harmon, and Mellissa Moe as connections. The mode names 1304 may illustrate names of the modes of operation associated with the therapeutic conditions (e.g., hypertension/blood pressure). The ratings 1306 may provide information to other users regarding the opinion of the users associated with the mode of treatment. The reviews 1308 may illustrate the number of reviews performed by other users. In one or more embodiments, the user John Smith may review the modes and provide ratings to the associated modes.

A mode creator 1310 may be a link that enables the user of the user interface (e.g., John Smith) to create a custom mode or to upload a mode created by the user (e.g., John Smith). A graphical representation of the medical instrument 1352 may illustrate a type of medical instrument for which a custom mode can be created. In one or more embodiments, a different type of medical instrument may be illustrated for which the user wants to create a custom mode via functions provided in the user interface (e.g., through graphical buttons, clicks, etc.).

Figure 14:
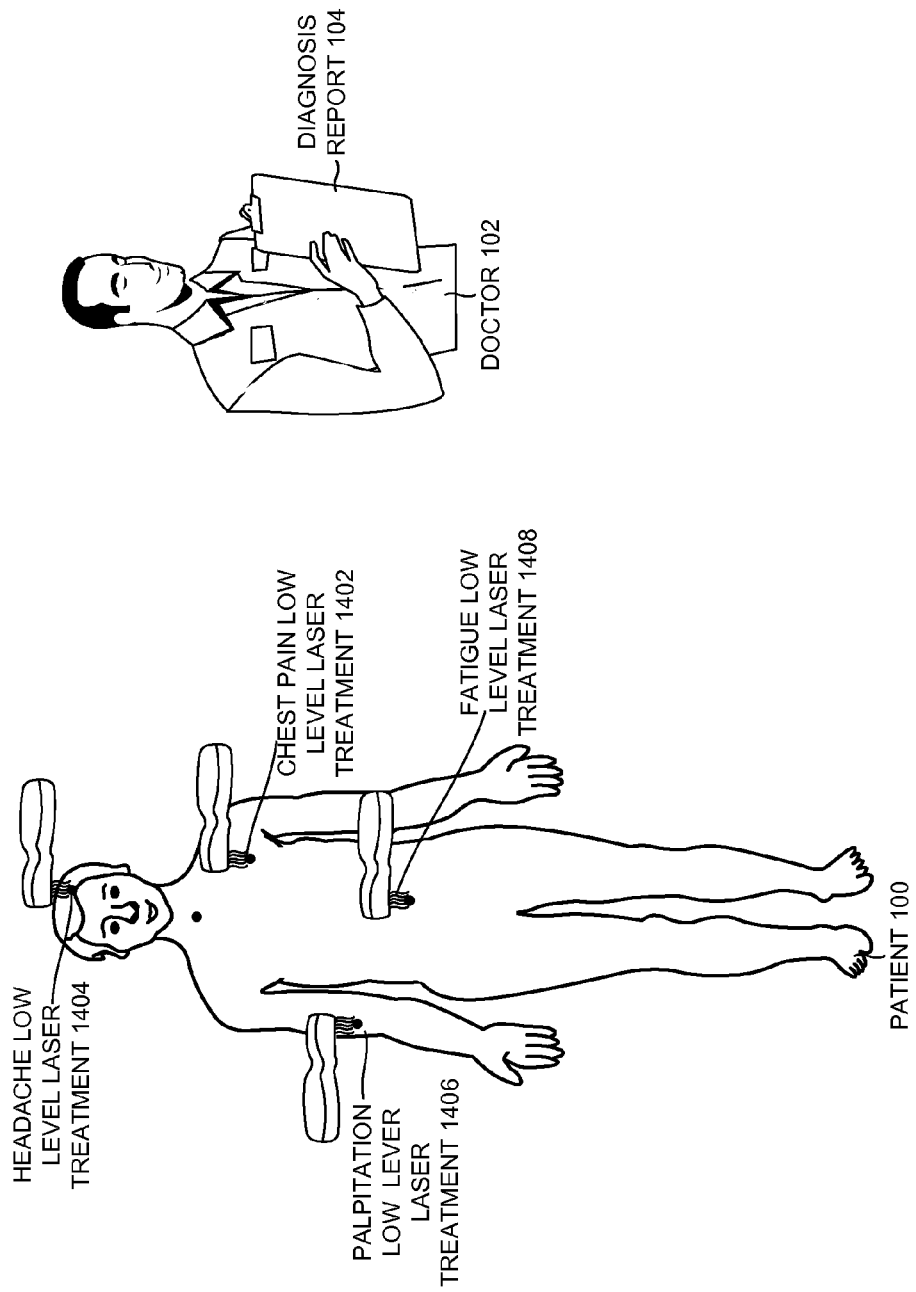
FIG. 14 illustrates a patient and a doctor diagnosing the patient using laser therapy, according to one or more embodiments.

FIG. 14 illustrates a doctor diagnosing a patient to generate a diagnosis report, according to an example embodiment. FIG. 14 herein illustrates the treatment being provided to the patient 100 through various application points $300_{1-N}$ for regulating a blood pressure and AGE in the blood. In operation 1402, low level radiation through the medical instrument 200A may be provided on the application point near chest to provide a relief to the patient suffering from chest pain caused due to high blood pressure/hyper tension. In operation 1404, low level laser radiation may be applied on the application point near the head to providing relief from headache/dizziness caused due to high blood pressure. In operation 1406, a low level laser radiation may be applied on an application point that may be on the inner crease of the elbow to provide relief from palpitation caused due to high blood pressure/hyper tension. In operation 1408, a low level laser treatment may be provided by applying radiation to an application point that is spot one hand width below and in line with the navel to provide relief to the patient from fatigue caused due to high blood pressure/hyper tension. Providing treatment to the application $300_{1-N}$ described here and other points may help in regulating blood pressure.

Figure 15:
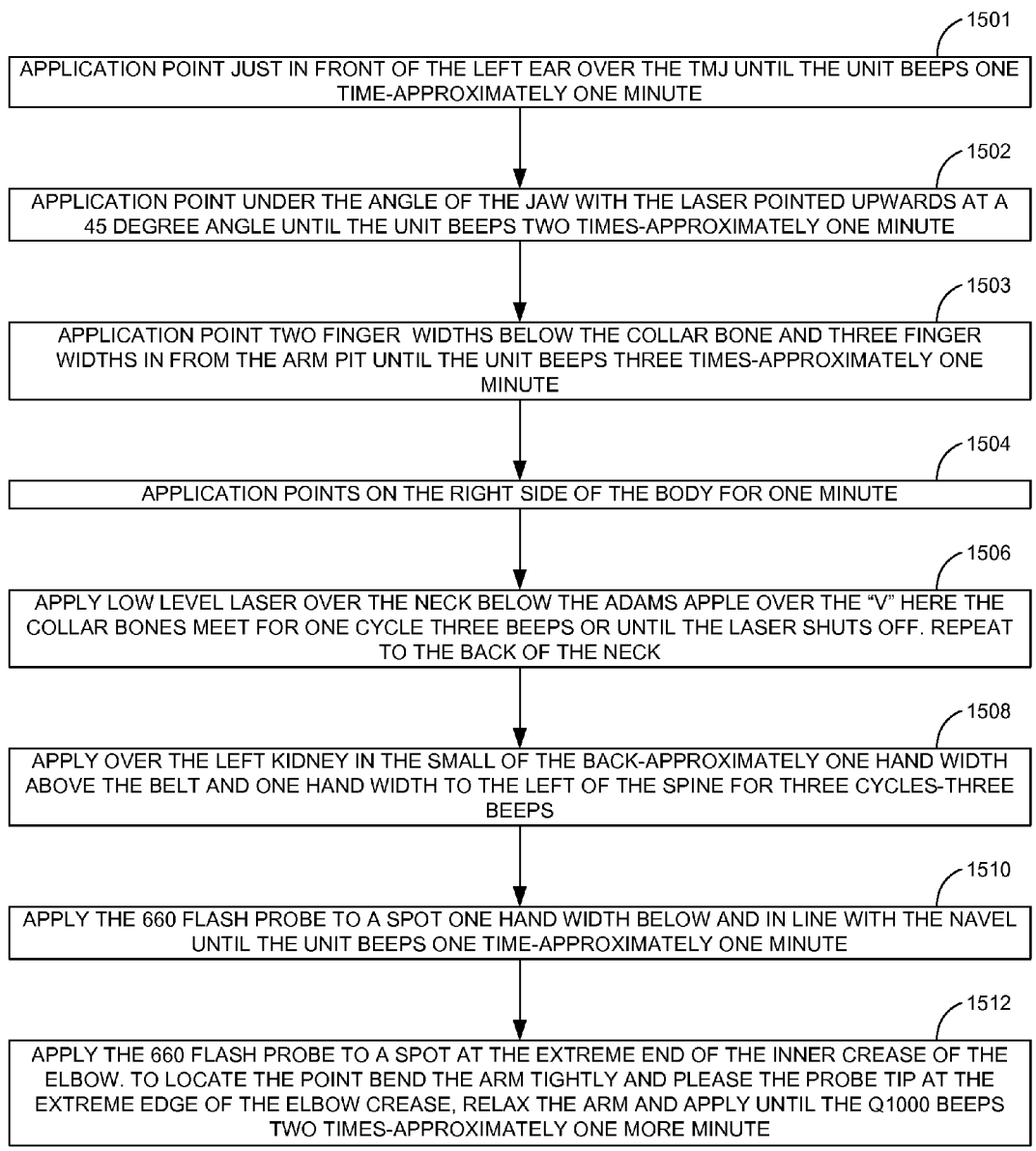
FIG. 15 is a process flow illustrating treatment steps involved in a laser based medical instrument, according to one or more embodiments.

FIG. 15 is a process flow illustrating the treatment steps 1500 involved in a laser based medical instrument, according to one or more embodiment. In one or more embodiments, in operation 1501, the laser based medical instrument may be used for generating radiation that may be radiated on patient's body parts over the application point. The application point may be in front of a left ear over a TMJ (as illustrated in FIG. 2A). The radiation may be applied until the unit beeps one time approximately after one minute has passed. In operation 1502, the radiation may be applied on an application point may be under the angle of the jaw with the laser radiation directed upwards at a 45 degree angle until the unit beeps two times approximately after one minute has passed (e.g., as illustrated in FIG. 2B). Radiation may be applied to an another application point that may be two finger widths below the collar bone and three finger widths in from the arm pit until the unit beeps three times approximately after one minute has passed as illustrated in operation 1503. The radiation may be applied on the application point that may be also on the right side of the body for one minute as illustrated in operation 1504.

In operation 1506, the low level laser may be applied over the neck below the Adams apple over the "V" where the collar bones meet for one cycle three beeps or until the laser shuts off. Operation 1506 may be repeated to the application point located on back of the neck. Radiation may be applied on the application point located in proximity to the kidney as illustrated in FIG. 3B. In operation 1508, radiation may be applied on the application point over the left kidney in the small of the back approximately one hand width above the belt and may be one hand width to the left of the spine (e.g., as illustrated in FIG. 3B) for three cycles three beeps. In operation 1510, radiation may be applied using a 660 flash probe (e.g., flash probe) may be applied to a spot one hand width below and in line with the navel until the unit beeps one time approximately for one minute. In operation 1512, radiation may be applied using the 660 flash probe may be applied to a spot at the extreme end of the inner crease of the elbow. To locate the aforementioned application point as in operation 1512 the arm may be bent tightly and please the probe tip at the extreme edge of the elbow crease, relax the arm. Radiation may be applied until the Q1000® by 2035, Inc.™ beeps two times approximately for one more minute.

FIG. 16 illustrates a treatment schedule 1600, according to one or embodiments. The treatment provided to the patient suffering from hypertension/high blood pressure may vary in its schedule. In an example embodiment, application of radiation 204 generated from a medical instrument (e.g., Q1000® by 2035, Inc.™) may be applied to the patient to provide treatment. The treatment may be provided every alternate day as per the prescription prescribed to the patient 100 by the doctor 102. A relief from the condition of hypertension/high blood pressure may be provided to the patient after the completion of the treatment. In an example embodiment, treatment may be provided on day 1, day 3, day 5, day 7, and day 9. Rest may be provided on alternate days.

Although the present embodiments have been described with reference to specific example embodiments, it will be evident that various modifications and changes may be made to these embodiments without departing from the broader spirit and scope of the various embodiments. Accordingly, the specification and drawings are to be regarded in an illustrative manner rather than a restrictive sense.

What is claimed:
1. A method comprising:
generating a first soliton wave through a laser diode of a first medical instrument at a first wavelength and at a first frequency;
generating a second soliton wave through a laser diode of a second medical instrument at a second wavelength and at a second frequency;
applying the first soliton wave to a first application point located two finger widths below the collar bone and three finger widths from the arm pit of a patient suffering from high-blood pressure, for a one minute duration;
repeating the application of the first soliton wave to the first application point for the one minute duration two more times in the same day;
applying the second soliton wave to a second application point located over the extreme outer edge of the patient's inner elbow crease, for a one minute duration;
repeating the application of the second soliton wave to the second application point for the one minute duration two more times in the same day;

coordinating the application of the first soliton wave and the second soliton wave through an algorithm that controls the generation of the first soliton wave of the first medical instrument and the generation of the second soliton wave of the second medical instrument; and reducing an advanced glycation end product (AGE) of the patient as a result of the application of the first soliton wave and the second soliton wave.

2. The method of claim 1, further comprising:

adjusting at least one of a pulsation power, a pulsation frequency, and a pulsation duration of the first medical instrument and the second medical instrument through a controller of the first medical instrument and a controller of the second medical instrument, respectively.

3. The method of claim 1, further comprising:

authenticating the first medical instrument based on an identifier associated with the medical instrument using a processor;

authenticating a user of the first medical instrument based on a password using the processor;

generating a graphical representation of the first medical instrument;

providing a set of rules associated with the first medical instrument based on the identifier associated with the first medical instrument and the user;

generating a first custom mode of operation of the first medical instrument based on a response of the user;

creating a name associated with the first custom mode of operation;

automatically programming the first medical instrument based on the first custom mode;

sharing the first custom mode with other users and other medical instruments based on the set of rules and a preference of the user;

authenticating the second medical instrument based on an identifier associated with the second medical instrument using the processor;

authenticating the user of the second medical instrument based on a password using the processor;

generating a graphical representation of the second medical instrument;

providing a set of rules associated with the second medical instrument based on the identifier associated with the second medical instrument and the user generating a second custom mode of operation of the second medical instrument based on a response of the user;

creating a name associated with the second custom mode of operation;

automatically programming the second medical instrument based on the second custom mode; and sharing the second custom mode with other users and other medical instruments based on the set of rules and a preference of the user.

4. The method of claim 1, further comprising:

applying the first soliton wave and the second soliton wave every other day up to sixty days.

* * * * *